US009097717B2

(12) United States Patent
Hosen et al.

(10) Patent No.: US 9,097,717 B2
(45) Date of Patent: Aug. 4, 2015

(54) METHODS OF KILLING MYELOMA STEM AND PRECURSOR CELLS BY ADMINISTERING ANTI-CD48 ANTIBODIES

(75) Inventors: Naoki Hosen, Osaka (JP); Haruo Sugiyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 13/263,206

(22) PCT Filed: Apr. 9, 2010

(86) PCT No.: PCT/JP2010/056449
§ 371 (c)(1),
(2), (4) Date: Nov. 10, 2011

(87) PCT Pub. No.: WO2010/117059
PCT Pub. Date: Oct. 14, 2010

(65) Prior Publication Data
US 2012/0045446 A1    Feb. 23, 2012

(30) Foreign Application Priority Data

Apr. 10, 2009    (JP) ................. 2009-096388

(51) Int. Cl.
| | | |
|---|---|---|
| *A61K 39/395* | (2006.01) | |
| *G01N 33/574* | (2006.01) | |
| *C07K 16/28* | (2006.01) | |
| *G01N 33/50* | (2006.01) | |
| *A61K 39/00* | (2006.01) | |

(52) U.S. Cl.
CPC ...... *G01N 33/57492* (2013.01); *C07K 16/2803* (2013.01); *G01N 33/5011* (2013.01); *A61K 2039/505* (2013.01); *C07K 2317/73* (2013.01); *C07K 2317/734* (2013.01); *G01N 2333/70503* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 2012/0022006 A1* | 1/2012 | Beltzer et al. | ............... | 514/21.4 |
| 2013/0011405 A1* | 1/2013 | Long et al. | ............... | 424/139.1 |
| 2013/0121913 A1* | 5/2013 | Hansen et al. | ............... | 424/1.49 |

FOREIGN PATENT DOCUMENTS

| | | |
|---|---|---|
| JP | 06-269293 | 9/1994 |
| JP | 2000-509015 | 7/2000 |
| JP | 2007-516213 | 6/2007 |
| WO | 9735614 | 10/1997 |
| WO | 9915902 | 4/1999 |
| WO | 2005014618 | 2/2005 |

OTHER PUBLICATIONS

Written Opinion of the International Searching Authority for the corresponding PCT/JP2010/056449; Nov. 15, 2011.*
Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., Embo J., 14: 2784-2794, 1995.*
Fauriat et al. (Leukemia 20: 732-733, 2006).*
Wei, Jiewei et al., Expression and characterisation of recombinant human CD48 and isolation of human anti-CD48 monoclonal antibody by phage display, J. Chem. Technol. Biotechnol., 2005, 80(7), p. 782-795.
Sun, Haiping et al., Preclinical Antitumor Activity of an Antibody against the Leukocyte Antigen CD48, Clin. Cancer Res., 1998, 4(4), p. 895-900.
Matsui, William et al., Characterization of clonogenic multiple myeloma cells, Blood, 2004, 103: pp. 2332-2336.
Matsui, William et al., Clonogenic Multiple Myeloma Progenitors, Stem Cell Properties, and Drug Resistance, Cancer Res., 2008, 68(1): pp. 190-197.
Kapoor, Prashant et al., Anti-CD20 monoclonal antibody therapy in multiple myeloma, Br. J. Haematol., 2008, 141: pp. 135-148.
Kawano, Michio et al., Autocrine generation and requirement of BSF-2/IL-6 for human multiple myelomas, Nature, 1988, vol. 332: pp. 83-85.
Klein, B et al., Paracrine rather than autocrine regulation of myeloma-cell growth and differentiation by interleukin-6, Blood, 1989, vol. 73: pp. 517-526.
Bataille, R., Biologic effects of anti-interleukin-6 murine monoclonal antibody in advanced multiple myeloma, Blood, 1995, vol. 86: pp. 685-691.
van Zaanen, H.C.T., et al., Chimaeric anti-interleukin 6 monoclonal antibodies in the treatment of advanced multiple myeloma: a phase I dose-escalating study, Br. J. Haematol., 1998, vol. 102: pp. 783-790.
Grossbard, Michael L., et al., Anti-B4-blocked ricin: a phase II trial of 7 day continuous infusion in patents with multiple myeloma, Br. J. Haematol., 1998, vol. 102: pp. 509-515.
McLain, D.A, et al., Biologic and Clinical Evaluation of Rituxan(RT) in the Management of Newly Diagnosed Multiple Myeloma (MM) In Patients (PTS), Blood, 1999, vol. 94 [Suppl.1]: 313a, Abstract#1400.
Maloney, David G. et al., Antibody Therapy for Treatment of Multiple Myeloma, Seminars in Hematology, 1999, vol. 36(1) [Suppl.]: pp. 30-33.

(Continued)

*Primary Examiner* — Phillip Gambel
(74) *Attorney, Agent, or Firm* — Roylance, Abrams, Berdo & Goodman, L.L.P.

(57) ABSTRACT

The present invention provides a therapeutic agent, for diseases in which neoplastic proliferation of plasma cells occurs, which is characterized by containing an anti-human CD48 monoclonal antibody and having cellular cytotoxicity to cells expressing human CD48; and the monoclonal antibody. In addition, the present invention provides a method for screening an active ingredient of a therapeutic agent for diseases in which neoplastic proliferation of plasma cells occurs, the method including the following processes:
(1) a process of sorting a substance that binds specifically to human CD48; and
(2) a process of sorting a substance having cellular cytotoxicity.

17 Claims, 8 Drawing Sheets

(56) References Cited

OTHER PUBLICATIONS

Huang, Yi-Wu, Anti-CD54 (ICAM-1) Has Antitumor Activity in SCID Mice with Human Myeloma Cells, Cancer Res., 1995, vol. 55: pp. 610-616.
Wijdenes, John et al., A plasmocyte selective monoclonal antibody (B-B4) recognizes syndecan-1, British Journal of Haematology, 1996, vol. 94: pp. 318-323.
Treon, Steven P. et al., Muc-1 Core Protein Is Expressed on Multiple Myeloma Cells and Is Induced by Dexamethasone, Blood, 1999, vol. 93: pp. 1287-1298.
Hosen, N., et al., Development of Antibody Therapy That Targets Myeloma Stem Cells, Program and Abstracts for the 33rd Meeting of the Japanese Society of Myeloma(Nov. 15, 2008).
Hosen, N., et al., Novel Target Antigens for Antibody Therapy for Multiple Myeloma, Program and Abstracts for the First Meeting of the Society of Immunotherapy for Hematological Malignancies (Aug. 17, 2009).
Hosen, N., et al., MMSC-1 is a novel target molecule for antibody therapy against both multiple myeloma progenitor cells and mature myeloma plasma cells, Abstract for Gordon Conference, Stem Cells & Cancer(Sep. 15, 2009).
Int'l Search Report for PCT/JP2010/056449, dated Jun. 1, 2010.
Sun, H. et al., Antitumour activity of a chimeric antibody against the leucocyte antigen CD48, Cancer Immunology, 2000, vol. 48, No. 10, pp. 595-602.
Smith, G. et al., Detection of a soluble form of the leukocyte surface antigen CD48 in plasma and its elevation in patients with lymphoid leukemias and arthritis, Journal of Clinical Immunology, 1997, vol. 17, No. 6, pp. 502-509.
Ozaki, S. et al., Immunotherapy of multiple myeloma with a monoclonal antibody directed against a plasma cell-specific antigen, HM1.24, Blood, 1997, vol. 90, No. 8, pp. 3179-3186.
Altvater, B. et al., 2B4 (CD244) signaling by recombinant antigen-specific chimeric receptors costimulates natural killer cell activation to leukemia and neuroblastoma cells, Clinical Cancer Research, 2009, vol. 15, No. 15, pp. 4857-4866.
Hosen, N. et al., CD48 as a novel molecular target for antibody therapy in multiple myeloma, British Journal of Haematology, 2012, vol. 156, No. 2, pp. 213-224.
Supplementary European Search Report dated Oct. 8, 2013 for EP Patent Application No. 10761758.1.

* cited by examiner

Fig. 6

Sequence of 1B4 VH

```
         10         20         30         40         50         60
CAGGTCCAGCTGCAGCAGTCTGGAGCTGAGCTGGTAAGGCCTGGGACTTCAGTGAAGATG
 Q   V   Q   L   Q   Q   S   G   A   E   L   V   R   P   G   T   S   V   K   M 70         80         90        100        110        120
TCCTGCAAGGCTGCTGGATACACCTTCACTAACTACTGGATAGGTTGGGTAAAGGAGAGG
 S   C   K   A   A  |G   Y   T   F   T   N   Y   W|  I   G   W   V   K   E   R
                    └──────── CDR1 ────────┘

130        140        150        160        170        180
CCTGGACATGGCCTTGAGTGGATTGGAGATATTTACCCTGGAGGTGGCTTTACTAACTAC
 P   G   H   G   L   E   W   I   G   D  |I   Y   P   G   G   G   F   T| N   Y
                                        └──────── CDR2 ────────┘

190        200        210        220        230        240
AATGAGAATTTCAAGGGCAAGGCCACACTGACTGCAGACACATCCTCCAGCACAGCCTAC
 N   E   N   F   K   G   K   A   T   L   T   A   D   T   S   S   S   T   A   Y 250        260        270        280        290        300
ATGCAGCTCAGCAGCCTGACATCTGAGGACTCTGCCATCTATCACTGTGCAAGAGGGATT
 M   Q   L   S   S   L   T   S   E   D   S   A   I   Y   H   C  |A   R   G   I 310        320        330        340        350
TACTACAATAGTAGCCCCTACTTTGACTCCTGGGGCCAAGGCACCACTCTCACA
 Y   Y   N   S   S   P   Y   F   D   S| W   G   Q   G   T   T   L   T
 └──────────── CDR3 ────────────┘
```

Fig. 7

Sequence of 1B4 VK

```
         10         20         30         40         50         60
GACATTGTGATGACCCAGTTTGCAGGTGTTGACGGAGACATTGTGATGACCCAGTCTCAC
 D  I  V  M  T  Q  F  A  G  V  D  G  D  I  V  M  T  Q  S  H 70         80         90        100        110        120
AAATTCATGTCCACATCAGTAGGAGACAGGGTCAGCATCACCTGCAAGGCCAGTCAGGAT
 K  F  M  S  T  S  V  G  D  R  V  S  I  T  C  K  A  S |Q  D 130        140        150        160        170        180
GTGAGTACTACTGTGGCCTGGTATCAGCAGAAACCAGGGCAATCTCCTAAACTACTGATT
 V  S  T  T| V  A  W  Y  Q  Q  K  P  G  Q  S  P  K  L  L  I
 CDR1

190        200        210        220        230        240
TATTCGGCATCCTACCGGTACACTGGAGTCCCTGATCGCTTCACTGGCAGTGGATCTGGG
 Y |S  A  S| Y  R  Y  T  G  V  P  D  R  F  T  G  S  G  S  G
    CDR2

250        260        270        280        290        300
ACGGATTTCACTTTCACCATCAGCAGTGTGCAGGCTGAAGACCTGGCAGTTTATTACTGT
 T  D  F  T  F  T  I  S  S  V  Q  A  E  D  L  A  V  Y  Y  C 310        320        330        340        350
CAGCAACATTATAGTACTCCTCCCACGTTCGGAGGGGGGACCAAGCTGGAAATAAAA
|Q  Q  H  Y  S  T  P  P  P  T| F  G  G  G  T  K  L  E  I  K
 CDR3
```

Fig. 8

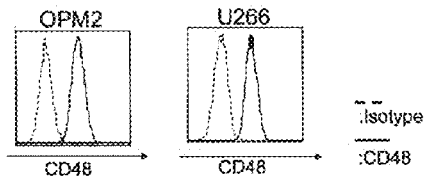

METHODS OF KILLING MYELOMA STEM AND PRECURSOR CELLS BY ADMINISTERING ANTI-CD48 ANTIBODIES

TECHNICAL FIELD

The present invention provides new finding concerning therapy for diseases in which neoplastic proliferation of plasma cells occurs. More particularly, the present invention provides finding concerning a novel target molecule effective for therapy for diseases in which neoplastic proliferation of plasma cells occurs. The present invention relates to a novel therapeutic agent and a novel therapeutic method, based on such finding, for diseases in which neoplastic proliferation of plasma cells occurs. In addition, the present invention relates to a method for screening an active ingredient for therapy for diseases in which neoplastic proliferation of plasma cells occurs. Further, the present invention relates to a reagent or kit for monitoring diseases in which neoplastic proliferation of plasma cells occurs.

BACKGROUND ART

Diseases in which neoplastic proliferation of plasma cells occurs are diseases in which plasma cells present in bone marrow become cancerous and proliferate into monoclonal cells. In the case of multiple myeloma that is a typical example of such diseases, abnormal plasma cells (myeloma cells) spread in bone marrow all over the body, and proliferate all over bone marrow in the whole body. The proliferation of the abnormal plasma cells (myeloma cells) causes various symptoms such as destruction of bone. The myeloma cells produce M protein, which is an abnormal immunoglobulin, and the M protein concentration rises in blood, whereby blood becomes viscous. M protein does not function as a proper antibody to recognize foreign substances, such as a pathogen that invades the body, and thus also causes decrease of immunity. These factors affect many organs and various signs occur. Typical signs are pain and damage of bone, hypercalcemia, renal damage, renal failure, anemia, etc.

Multiple myeloma occupies about 1% of all the cancers and occupies a little more than 10% of all the hematological malignant tumors. Thus, an effective therapeutic agent therefor is called for. At present, chemotherapies, such as combined use of merphalan and prednisone and use of thalidomide, and hematopoietic stem cell transplantation are mainly performed as therapy for multiple myeloma. However, in most cases, myeloma cells acquire resistance to these chemotherapeutic agents soon. Thus, in the existing therapeutic approach, the average survival time after development of symptoms is about three to five years, and the prognoses of myeloma patients are actually severe. Since these therapeutic agents do not act specifically on only target tumor cells, they exhibit toxicity also to normal cells and there is a problem that serious side effects are produced as a result.

One of the reasons why diseases in which neoplastic proliferation of plasma cells occurs, such as multiple myeloma, are very intractable is thought to be that myeloma stem cells, which are precursors of myeloma plasma cells, are not eliminated by therapy (Non-Patent Literature 1 and Non-Patent Literature 2). Since myeloma stem cells are present in a $CD19^+$ cell fraction, therapy for multiple myeloma using an antibody (rituximab) to CD20 highly-expressed in the same pattern as CD19 has been attempted, but there has been no report that a sufficient therapeutic efficacy is obtained (Non-Patent Literature 3). In addition, development of therapy for multiple myeloma using an antibody has been attempted. For example, it is thought that IL-6 is a major proliferator for multiple myeloma cells (Non-Patent Literature 4 and Non-Patent Literature 5), and development of a therapeutic agent for multiple myeloma using a neutralizing antibody to IL-6 or an IL-6 receptor was attempted for the purpose of preventing an IL-6 signal transduction system. However, although proliferation inhibition of myeloma cells was observed in patients with plasma cell leukemia, tumors recurred and clinical efficacy has not been obtained (Non-Patent Literature 6 and Non-Patent Literature 7). Further, there have been reports that some antigen molecules (e.g., CD19 (Non-Patent Literature 8), CD20 (Non-Patent Literature 9), CD38 (Non-Patent Literature 10), CD54 (Non-Patent Literature 11), CD138 (Non-Patent Literature 12), Muc-1 (Non-Patent Literature 13), etc.) can be effective targets in antibody therapy, but a practical therapeutic agent has not been developed.

CITATION LIST

Non-Patent Literature

NPL 1: Matsui, W., et al., Blood, 2004. 103:2332-6.
NPL 2: Matsui, W., et al., Cancer Res, 2008. 68:190-7.
NPL 3: Kapoor, P., et al., Br J Haematol., 2008. 141:135-48
NPL 4: Kawano et al., Nature., 1988. Vol. 332: 83
NPL 5: Klein et al., Blood., 1989. Vol. 73: 517
NPL 6: Bataille et al., Blood., 1995. Vol. 86: 685-691
NPL 7: Van Zaanen et al., Br J Haematol., 1998 Vol. 102:783
NPL 8: Grossbard et al., Br J Haematol., 1998. Vol. 102:509
NPL 9: Hussein et al., Blood., 1999. Blood., 1999, Vol. 94 [Suppl. 1]:313
NPL 10: Maloney et al., Semin Hematol., 1999 Vol. 36 [Suppl.]:30
NPL 11: Huang et al., Cancer Res., 1995 Vol. 55: 610
NPL 12: Wijdenes et al., Br J Haematol., 1996 Vol. 94: 318
NPL 13: Treon et al., Blood., 1999 Vol. 93: 1287

SUMMARY OF INVENTION

Technical Problem

An object of the present invention is to provide a novel therapeutic agent effective for therapy for diseases in which neoplastic proliferation of plasma cells occurs. In addition, an object of the present invention is to provide a method for screening an active ingredient of a therapeutic agent for diseases in which neoplastic proliferation of plasma cells occurs. Further, an object of the present invention is to provide novel findings concerning therapy for diseases in which neoplastic proliferation of plasma cells occurs.

Solution to Problem

Under the circumstances described above, in order to achieve radical therapy for diseases in which neoplastic proliferation of plasma cells occurs, the inventors of the present invention conducted thorough research concerning a therapeutic method for multiple myeloma as a typical example. As a result, the inventors found that as shown in Examples 3 and 4 described below, human CD48 is a molecule that is consistently expressed on the cell surfaces of myeloma stem cells and myeloma precursor cells and is not expressed in hematopoietic stem cells. In addition, the inventors found that human CD48 continues to be highly expressed not only in myeloma stem cells and myeloma precursor cells but also in mature myeloma plasma cells. Based on the findings, the inventors of the present invention further conducted research, prepared a monoclonal antibody that has cellular cytotoxicity and specifically recognizes human CD48, and confirmed that by administering the antibody into animals in which myeloma cells are transplanted proliferation of the myeloma cells is inhibited. On the basis of theses results, the inventors confirmed that radical therapy for diseases in which neoplastic proliferation of plasma cells occurs, such as multiple myeloma, is possible by targeting cells expressing human CD48 and killing the cells or inhibiting proliferation of the cells. The present invention is completed on the basis of the finding described above.

In other words, the present invention includes inventions of the following aspects.

I. Therapeutic Agent for Diseases in which Neoplastic Proliferation of Plasma Cells Occurs (I-1) A therapeutic agent for diseases in which neoplastic proliferation of plasma cells occurs, the therapeutic agent containing a monoclonal antibody to human CD48 and having cellular cytotoxicity to cells expressing human CD48.

(I-2) The therapeutic agent according to (I-1), wherein the monoclonal antibody to human CD48 (antihuman CD48 monoclonal antibody) has cellular cytotoxicity.

(I-3) The therapeutic agent according to (I-1), wherein the anti-human CD48 monoclonal antibody is bound to a substance having cellular cytotoxicity.

(I-4) A therapeutic agent for diseases in which neoplastic proliferation of plasma cells occurs, the therapeutic agent containing, as an active ingredient, a product in which a substance having cellular cytotoxicity is bound to the anti-human CD48 monoclonal antibody.

(I-5) A therapeutic agent for diseases in which neoplastic proliferation of plasma cells occurs, the therapeutic agent containing a substance having cellular cytotoxicity and an anti-human CD48 monoclonal antibody as its carrier.

(I-6) The therapeutic agent according to any one of (I-3) to (I-5), wherein the substance having cellular cytotoxicity is a substance having an anticancer effect.

(I-7) The therapeutic agent according to any one of (I-1) to (I-6), wherein the anti-human CD48 monoclonal antibody is any one of antibodies of the following (a) to (c):

(a) a monoclonal antibody that has a heavy chain variable region comprising an amino acid sequence shown in SEQ ID NO: 1 and a light chain variable region comprising an amino acid sequence shown in SEQ ID NO: 3, and that binds specifically to human CD48, (b) a monoclonal antibody that recognizes the same epitope as the monoclonal antibody described in (a), and (c) a monoclonal antibody that has a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and that binds specifically to human CD48.

(I-8) The therapeutic agent according to any one of (I-1) to (I-6), wherein the anti-human CD48 monoclonal antibody is any one of antibodies of the following (d) to (f):

(d) a monoclonal antibody that has a heavy chain variable region comprising an amino acid sequence shown in SEQ ID NO: 1, a light chain variable region comprising an amino acid sequence shown in SEQ ID NO: 3, a heavy chain constant region comprising an amino acid sequence shown in SEQ ID NO: 5, and a light chain constant region comprising an amino acid sequence shown in SEQ ID NO: 6, and that binds specifically to human CD48, (e) a monoclonal antibody that recognizes the same epitope as the monoclonal antibody described in (d), and (f) a monoclonal antibody comprising an amino acid sequence having an identity of 80% or higher to an entire amino acid sequence of the monoclonal antibody described in (d), having a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and having a specific binding property to human CD48.

(I-9) The therapeutic agent according to any one of (I-1) to (I-8), wherein a disease in which neoplastic proliferation of plasma cells occurs is multiple myeloma.

II. Method for Screening an Active Ingredient of a Therapeutic Agent for Diseases in which Neoplastic Proliferation of Plasma Cells Occurs (II-1) A method for screening an active ingredient of a therapeutic agent for diseases in which neoplastic proliferation of plasma cells occurs, the method comprising the following processes:

(1) a process of sorting a substance that binds specifically to human CD48; and (2) a process of sorting a substance having cellular cytotoxicity.

III. Method for Identifying Neoplastic Plasma Cells (III-1) A method for identifying neoplastic plasma cells, the method comprising a process of causing a monoclonal antibody to human CD48 (anti-human CD48 monoclonal antibody) to act on a sample taken from a patient afflicted with a disease in which neoplastic proliferation of plasma cells occurs.

(III-2) The method according to (III-1), wherein the anti-human CD48 monoclonal antibody is any one of antibodies of the following (a) to (c):

(a) a monoclonal antibody that has a heavy chain variable region comprising an amino acid sequence shown in SEQ ID NO: 1 and a light chain variable region comprising an amino acid sequence shown in SEQ ID NO: 3, and that has a specific binding property to human CD48, (b) a monoclonal antibody that recognizes the same epitope as the monoclonal antibody described in (a), and (c) a monoclonal antibody that has a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and that binds specifically to human CD48.

(III-3) The method according to (III-1) or (III-2), wherein the anti-human CD48 monoclonal antibody is any one of antibodies of the following (d) to (f):

(d) a monoclonal antibody that has a heavy chain variable region comprising an amino acid sequence shown in SEQ ID NO: 1, a light chain variable region comprising an amino acid sequence shown in SEQ ID NO: 3, a heavy chain constant region comprising an amino acid sequence shown in SEQ ID NO: 5, and a light chain constant region comprising an amino acid sequence shown in SEQ ID NO: 6, and that binds specifically to human CD48, (e) a monoclonal antibody that recognizes the same epitope as the monoclonal antibody described in (d), and (f) a monoclonal antibody that has an amino acid sequence having an identity of 80% or higher to an entire amino acid sequence of the monoclonal antibody described in (d), that has a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and that binds specifically to human CD48.

IV. Reagent or Kit for Monitoring Progression of or Therapeutic Effect for Diseases in which Neoplastic Proliferation of Plasma Cells Occurs (IV-1) A reagent or kit for monitoring diseases in which neoplastic proliferation of plasma cells occurs, the reagent or kit comprising a monoclonal antibody to human CD48 (an anti-human CD48 monoclonal antibody).

(IV-2) The reagent or kit according to (III-1), wherein the anti-human CD48 monoclonal antibody is any one of antibodies of the following (a) to (c):

(a) a monoclonal antibody that has a heavy chain variable region comprising an amino acid sequence shown in SEQ ID NO: 1 and a light chain variable region comprising an amino acid sequence shown in SEQ ID NO: 3, and that binds specifically to human CD48, (b) a monoclonal antibody that recognizes the same epitope as the monoclonal antibody described in (a), and (c) a monoclonal antibody that has a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and that binds specifically to human CD48.

(IV-3) The reagent or kit according to (IV-1) or (IV-2), wherein the anti-human CD48 monoclonal antibody is any one of antibodies of the following (d) to (f):

(d) a monoclonal antibody that has a heavy chain variable region comprising an amino acid sequence shown in SEQ ID NO: 1, a light chain variable region comprising an amino acid sequence shown in SEQ ID NO: 3, a heavy chain constant region comprising an amino acid sequence shown in SEQ ID NO: 5, and a light chain constant region comprising an amino acid sequence shown in SEQ ID NO: 6, and that binds specifically to human CD48, (e) a monoclonal antibody that recognizes the same epitope as the monoclonal antibody described in (d), and (f) a monoclonal antibody that has an amino acid sequence having an identity of 80% or higher to an entire amino acid sequence of the monoclonal antibody described in (d), that has a heavy chain variable region comprising an amino acid sequence having an identity of 90% or higher to the amino acid sequence shown in SEQ ID NO: 1 and a light chain variable region comprising an amino acid sequence having an identity of 90% or higher to the amino acid sequence shown in SEQ ID NO: 3, and that binds specifically to human CD48.

V. Anti-Human CD48 Monoclonal Antibody (V-1) A monoclonal antibody to human CD48 (an anti-human CD48 monoclonal antibody) that has a heavy chain variable region comprising an amino acid sequence shown in SEQ ID NO: 1 and a light chain variable region comprising an amino acid sequence shown in SEQ ID NO: 3.

(V-2) An anti-human CD48 monoclonal antibody that recognizes the same epitope as the monoclonal antibody according to the (V-1)

(V-3) An anti-human CD48 monoclonal antibody that has a heavy chain variable region comprising an amino acid sequence having an identity of 90% or higher to an amino acid sequence shown in SEQ ID NO: 1 and a light chain variable region comprising an amino acid sequence having an identity of 90% or higher to an amino acid sequence shown in SEQ ID NO: 3, and that binds specifically to human CD48.

(V-4) A monoclonal antibody that has a heavy chain variable region comprising an amino acid sequence shown in SEQ ID NO: 1, a light chain variable region comprising an amino acid sequence shown in SEQ ID NO: 3, a heavy chain constant region comprising an amino acid sequence shown in SEQ ID NO: 5, and a light chain constant region comprising an amino acid sequence shown in SEQ ID NO: 6, and that binds specifically to human CD48.

(V-5) An anti-human CD48 monoclonal antibody that recognizes the same epitope as the monoclonal antibody described in (V-4).

(V-6) A monoclonal antibody that has an amino acid sequence having an identity of 80% or higher to an entire amino acid sequence of the monoclonal antibody described in (V-4), that has a heavy chain variable region comprising an amino acid sequence having an identity of 90% or higher to an amino acid sequence shown in SEQ ID NO: 1 and a light chain variable region comprising an amino acid sequence having an identity of 90% or higher to an amino acid sequence shown in SEQ ID NO: 3, and that binds specifically to human CD48.

VI. Therapeutic Method for Diseases in which Neoplastic Proliferation of Plasma Cells Occurs (VI-1) A therapeutic method for diseases in which neoplastic proliferation of plasma cells occurs, the method comprising a process of administrating a therapeutic agent according to any one of (I-1) to (I-9) to a patient afflicted with a disease in which neoplastic proliferation of plasma cells occurs.

(VI-2) The therapeutic method according to (VI-1), wherein a disease in which neoplastic proliferation of plasma cells occurs is multiple myeloma.

VII. Use for Therapy for Diseases in which Neoplastic Proliferation of Plasma Cells Occurs (VII-1) A monoclonal antibody to human CD48 (an anti-human CD48 monoclonal antibody) used for therapy for diseases in which neoplastic proliferation of plasma cells occurs.

(VII-2) The anti-human CD48 monoclonal antibody according to (VII-1), wherein the anti-human CD48 monoclonal antibody has a heavy chain variable region comprising an amino acid sequence shown in SEQ ID NO: 1 and a light chain variable region comprising an amino acid sequence shown in SEQ ID NO: 3, and binds specifically to human CD48.

(VII-3) The anti-human CD48 monoclonal antibody according to (VII-1), wherein the anti-human CD48 monoclonal antibody recognizes the same epitope as the monoclonal antibody described in the (VII-2).

(VII-4) The anti-human CD48 monoclonal antibody according to (VII-1), wherein the anti-human CD48 monoclonal antibody is a monoclonal antibody having a heavy chain variable region that has an amino acid sequence having an identity of 90% or higher to an amino acid sequence shown in SEQ ID NO: 1 and a light chain variable region comprising an amino acid sequence having an identity of 90% or higher to an amino acid sequence shown in SEQ ID NO: 3, and that binds specifically to human CD48.

(VII-5) The anti-human CD48 monoclonal antibody according to (VII-1), wherein the anti-human CD48 monoclonal antibody is a monoclonal antibody that has a heavy chain variable region comprising an amino acid sequence shown in SEQ ID NO: 1, a light chain variable region comprising an amino acid sequence shown in SEQ ID NO: 3, a heavy chain constant region comprising an amino acid sequence shown in SEQ ID NO: 5, and a light chain constant region comprising an amino acid sequence shown in SEQ ID NO: 6, and that binds specifically binding property to human CD48.

(VII-6) The anti-human CD48 monoclonal antibody according to (VII-1), wherein the anti-human CD48 monoclonal antibody is a monoclonal antibody that recognizes the same epitope as the monoclonal antibody described in (VII-5).

(VII-7) The anti-human CD48 monoclonal antibody according to (VII-1), wherein the anti-human CD48 monoclonal antibody is a monoclonal antibody that has an amino acid sequence having an identity of 80% or higher to an entire amino acid sequence of the monoclonal antibody described in (VII-5), that has a heavy chain variable region comprising an amino acid sequence having an identity of 90% or higher to an amino acid sequence shown in SEQ ID NO: 1 and a light chain variable region comprising an amino acid sequence having an identity of 90% or higher to an amino acid sequence shown in SEQ ID NO: 3, and that binds specifically to human CD48.

(VII-8) The anti-human CD48 monoclonal antibody according to any of (VII-1) to (VII-7), wherein the anti-human CD48 monoclonal antibody has cellular cytotoxicity.

(VII-9) Use of an anti-human monoclonal antibody, for producing a therapeutic agent for diseases in which neoplastic proliferation of plasma cells occurs.

Advantageous Effects of Invention

According to the therapeutic agent and the therapeutic method of the present invention, by targeting CD48, not only mature myeloma cells but also a series of undifferentiated myeloma stem cells and myeloma precursor cells that have a high possibility of differentiating into myeloma cells in the future can be targeted. Then, by killing and/or inhibiting proliferation of these target cells, myeloma stem cells and myeloma precursor cells can be blocked from differentiating into myeloma cells. Further, since CD48 is expressed in mature myeloma plasma cells as well, according to the therapeutic agent and the therapeutic method of the present invention, the mature myeloma plasma cells is killed and/or proliferation thereof is inhibited. Thus, the therapeutic agent of the present invention can be used effectively for therapy, particularly radical therapy, for diseases in which neoplastic proliferation of plasma cells occurs, such as multiple myeloma. In addition, the therapeutic agent of the present invention has low affinity to hematopoietic stem cells, and thus a safety problem caused by hematopoietic stem cells being attacked is alleviated.

According to the screening method of the present invention, use of a binding property to human CD48 and cellular cytotoxicity as indicators makes it possible to easily and efficiently obtain an active ingredient for therapy for diseases in which neoplastic proliferation of plasma cells occurs. In addition, the method of the present invention allows neoplastic plasma cells to be identified easily and more accurately, and makes it possible to monitor diseases in which neoplastic proliferation of plasma cells occurs.

BRIEF DESCRIPTION OF DRAWINGS

FIG. 6 shows the base sequence and the amino acid sequence of the heavy chain variable region and the positions of CDR1 to 3 of an anti-human CD48 monoclonal antibody (1B4).

FIG. 7 shows the base sequence and the amino acid sequence of the light chain (κ chain) variable region and the positions of CDR1 to 3 of the anti-human CD48 monoclonal antibody (1B4).

FIG. 8 shows expression of the CD48 molecule in myeloma cell lines OPM2 and U266, wherein a signal by staining in Isotype (mouse IgG2a) is shown as control.

DESCRIPTION OF EMBODIMENTS

Classification and Definition of Myeloma Stem Cell and Myeloma Precursor Cell

Figure 1:
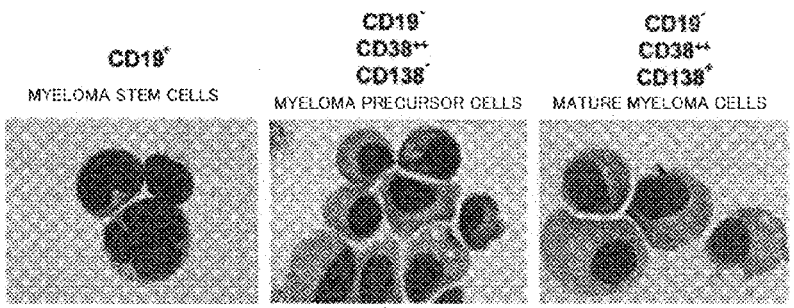
FIG. 1 shows the morphological features of cells contained in a myeloma stem cell fraction, a myeloma precursor cell fraction, and a mature myeloma cell fraction, by May-Giemsa staining.

In the present specification, a myeloma stem cell and a myeloma precursor cell refer to cells that are at a stage prior to differentiation into mature myeloma plasma cells (neoplastic plasma cells) and that have a property of differentiating into myeloma plasma cells later. Myeloma stem cells and myeloma precursor cells can be classified according to the stages of their differentiation. FIG. 1 shows pictures of myeloma stem cells, myeloma precursor cells, and mature myeloma plasma cells that are stained with May-Giemsa. Bone marrow B cells that have become myeloma stem cells turn into mature myeloma plasma cells through myeloma precursor cells later.

A "myeloma stem cell (CD19$^+$ myeloma stem cell)" is characterized by expression of CD19, which is a surface antigen molecule. Thus, in the present specification, a myeloma stem cell may be described as "CD19+ cell".

A "myeloma precursor cell (CD19⁻CD38++CD138⁻ myeloma precursor cell)" is a precursor cell that is differentiated from a CD19+ myeloma stem cell and that is at a stage immediately prior to differentiation into a myeloma plasma cell. CD38 is highly expressed therein, but the "myeloma precursor cell" is characterized by non-expression of CD138, which is a specific marker for mature plasma cells. Meanwhile, no expression of CD19 is observed. Thus, the myeloma precursor cell may be described as "CD19⁻CD38++CD138⁻ cell".

In general, the "myeloma plasma cell" is also referred to as myeloma cell, and is a cell that produces M protein, which is an abnormal immunoglobulin. In the myeloma plasma cell, in addition to CD38 being highly expressed, CD138 is expressed. Meanwhile, no expression of CD19 is observed. Thus, the myeloma plasma cell may be described as "CD19⁻CD38++CD138+ cell". In the present specification, the myeloma stem cell, the myeloma precursor cell, and the myeloma plasma cell also refer to a tumor stem cell, a tumor precursor cell, and a neoplastic plasma cell, respectively, in diseases in which neoplastic proliferation of plasma cells occurs, other than multiple myeloma.

A "hematopoietic stem cell" is a cell that can differentiate into any hematopoietic cell. The hematopoietic stem cell is characterized by expression of CD34. Thus, in the present specification, the hematopoietic stem cell may be described as "CD34+ cell".

In the present invention, diseases in which neoplastic proliferation of plasma cells occurs are diseases that are characterized by neoplastic proliferation of abnormal plasma cells and increase of abnormal proteins secreted from them. Particular examples of neoplastic proliferation of plasma cells include multiple myeloma, plasmacytic leukemia, plasmocytoma, H chain diseases, and systemic AL type amyloidosis. A disease to be treated by a therapeutic agent of the present invention is not particularly limited as long as it is a disease in which neoplastic proliferation of plasma cells occurs, but is preferably multiple myeloma.

I. Therapeutic Agent and Therapeutic Method for Diseases in which Neoplastic Proliferation of Plasma Cells Occurs The therapeutic agent of the present invention for diseases in which neoplastic proliferation of plasma cells occurs contains an anti-human CD 48 monoclonal antibody and has cellular cytotoxicity to cells expressing human CD48.

I-I. Monoclonal Antibody to Human CD48

The monoclonal antibody to human CD48 (hereinafter, may be referred to as "anti-human CD48 monoclonal antibody") is a monoclonal antibody that binds specifically to human CD48. As shown in Examples 3 and 4 described below, human CD48 is consistently expressed on the cell surfaces of myeloma stem cells, myeloma precursor cells, and myeloma plasma cells, but is not expressed at all or is slightly expressed in hematopoietic stem cells. Thus, by targeting human CD48, myeloma stem cells, myeloma precursor cells, and myeloma plasma cells can be targeted without targeting hematopoietic stem cells which supply normal lymphocytes and the like. The anti-human CD48 monoclonal antibody is an antibody that binds specifically to human CD48, and thus can specifically recognize and bind to myeloma stem cells, myeloma precursor cells, and myeloma plasma cells. Therefore, the anti-human CD48 monoclonal antibody is an antibody suitable for targeting cells to be treated in therapy, preferably radical therapy, for diseases in which neoplastic proliferation of plasma cells occurs, such as multiple myeloma. In other words, by combining the anti-human CD48 monoclonal antibody with cellular cytotoxicity, the activity can be caused to act specifically on myeloma stem cells, myeloma precursor cells, and myeloma plasma cells.

The anti-human CD48 monoclonal antibody intended by the present invention include various antibodies, as long as they have a property of recognizing and binding to myeloma stem cells, myeloma precursor cells, and myeloma plasma cells due to affinity to human CD48 as described above. For example, the anti-human CD48 monoclonal antibody may be a modified antibody such as a humanized antibody, or may be its fragment (e.g., Fab, Fab', F(ab')$_2$, scFv, etc.).

A preferable anti-human CD48 monoclonal antibody is, for example, a monoclonal antibody produced in Example 4 described below (hereinafter, may be referred to as "1B4 antibody"), has an amino acid sequence shown in SEQ ID NO: 1 as the amino acid sequence of a heavy chain variable region, has an amino acid sequence shown in SEQ ID NO: 3 as the amino acid sequence of a light chain variable region, has an amino acid sequence shown in SEQ ID NO: 5 as the amino acid sequence of a heavy chain constant region, and has an amino acid sequence shown in SEQ ID NO: 6 as the amino acid sequence of a light chain constant region. The 1B4 antibody can be produced on the basis of its sequence information using a genetic engineering technique or a chemical peptide synthesis method known in the technical field.

Other preferable monoclonal antibodies are antibodies that recognize the same epitope as the 1B4 monoclonal antibody, and, in particular, monoclonal antibodies that can bind to the same epitope. Whether or not an antibody recognizes the same epitope as another antibody can be confirmed by competition of these antibodies to epitope. Competition between antibodies can be assessed by a competitive binding assay, and examples of its means include an enzyme-linked immunosorbent assay (ELISA), a fluorescent-energy-transfer measuring method (FRET) and fluorometric microvolume assay technology (FMAT (registered trademark)). The amount of the antibody binding to an antigen indirectly correlates with the binding capacity of a candidate competitive antibody (a test antibody) that competes for binding to the same epitope. In other words, as the amount and affinity of the test antibody to the same epitope increases, the amount of the antibody binding to the antigen decreases and the amount of the test antibody binding to the antigen increases. More particularly, the appropriately-labeled antibody and an antibody that is to be assessed are simultaneously added to the antigen, and the binding antibody is detected using the label. The amount of the antibody binding to the antigen can easily be measured when the antibody is previously labeled. This labeling is not particularly limited, but a labeling method suitable for the technique is selected. Particular examples of the labeling method include fluorescence labeling, radiolabeling, and enzyme labeling.

For example, the fluorescence-labeled antibody and the unlabeled antibody or the test antibody are simultaneously added to beads obtained by solidifying human CD48, and the labeled antibody is detected by fluorometric microvolume assay technology.

The "antibody that recognizes the same epitope" herein is an antibody that is a test antibody that can decrease the binding amount of the labeled antibody by at least 50% with a concentration that is higher, by normally 100 times, preferably 80 times, more preferably 50 times, even more preferably 30 times, and much more preferably 10 times, than a concentration ($IC_{50}$) of the unlabeled antibody with which the binding amount of the labeled antibody is decreased by 50% due to binding of the unlabeled antibody.

Examples of such monoclonal antibodies include the following antibodies (A) and (B).

(A) Antibody: an antibody comprising an amino acid sequence that is an amino acid sequence of the 1B4 antibody in which one or a plurality of amino acids are substituted, deleted, inserted, and/or added.

(B) Antibody: an antibody comprising an amino acid sequence having an identity of 80% or higher to the entire amino acid sequence of the 1B4 antibody.

In the above antibody (A), the plurality of amino acids are, for example, 2 to 30 amino acids, preferably 2 to 15 amino acids, more preferably 2 to 10 amino acids, even more preferably 2 to 5 amino acids, and much more preferably 2 or 3 amino acids. The positions at which the amino acids are substituted, deleted, inserted, and/or added are not limited as long as the antibody specifically recognizes the same epitope as the 1B4 antibody, but the positions are preferably regions other than CDR1 to 3 in the heavy chain and the light chain shown in FIGS. 6 and 7 and more preferably constant regions. The substitution, deletion, insertion, or addition of one or a plurality of amino acids can be performed according to a known method described in Molecular Cloning, A Laboratory Manual, Second Edition (Cold Spring Harbor Laboratory Press, 1989) or the like.

The identity of the amino acid sequence of the above antibody (B) is preferably equal to or higher than 85%, more preferably equal to or higher than 90%, even more preferably equal to or higher than 95%, and particularly preferably equal to or higher than 98%. In a preferred embodiment, the above antibody (B) has a heavy chain variable region having an identity of 90% or higher, preferably 95% or higher, more preferably 97% or higher, and particularly preferably 98% or higher, to the amino acid sequence shown in SEQ ID NO: 1, and has a light chain variable region having an identity of 90% or higher, preferably 95% or higher, more preferably 97% or higher, and particularly preferably 98% or higher, to the amino acid sequence of SEQ ID NO: 3. In still another preferred embodiment, the above antibody (B) has the same amino acid sequence as the 1B4 antibody in the CDR1 to 3 of the heavy chain and the light chain.

An identity of amino acids can be calculated using an analysis tool (e.g., software such as FASTA, BLAST, PSI-BLAST, and SSEARCH) that is commercially available or can be used through the Internet. For example, main initial conditions generally used for BLAST searching are as follows. Particularly, in Advanced BLAST 2.1, blastp is used as a program, an Expect value is set to 10, all Filters are set to OFF, BLOSUM62 is used as Matrix, Gap existence cost, Per residue gap cost, and Lambda ratio are set to 11, 1, 0.85 (defaults), respectively, other various parameters are also set to defaults, and searching is performed, whereby the value (%) of an identity of an amino acid sequence can be calculated.

The anti-human CD48 monoclonal antibody may be an antibody belonging to any immunoglobulin class and subclass, but is preferably an antibody belonging to human immunoglobulin class and subclass. The class and subclass are preferably immunoglobulin G (IgG) and more preferably human IgG1.

The anti-human CD48 monoclonal antibody can be produced according to a known method described in Molecular Cloning, A Laboratory Manual, Second Edition (Cold Spring Harbor Laboratory Press, 1989) or the like. A particular production method will be described below. In addition, some anti-human CD48 monoclonal antibodies are commercially available, and they can also be selected/prepared as appropriate and used.

In light of reducing antigenicity to human, the anti-human CD48 monoclonal antibody is preferably a humanized antibody. The humanized antibody is a chimeric antibody that is obtained by substituting, with the amino acid sequence of a human immunoglobulin, a portion of a non-human animal antibody other than the variable region (or the super variable region) and that has reduced antigenicity to human while maintaining its affinity to human CD48. The humanized monoclonal antibody can be produced according to a known method.

Method for Producing Anti-Human CD48 Monoclonal Antibody

The anti-human CD48 monoclonal antibody can be produced by immunizing an animal with human CD48. Hereinafter, a method for producing a monoclonal antibody to human CD48 will be described more particularly.

(1) Obtaining of Human CD48

First, a DNA fragment containing a cDNA coding for human CD48 is inserted into an appropriate expression vector to create a recombinant vector. This vector is introduced into a host cell suitable for the expression vector, to obtain a transformant. The DNA coding for human CD48 is known (e.g., database NCBI Genbank, accession number NM 001778.2) and is also commercially available. As the host cell, arbitrary cells, such as *Escherichia coli*, yeast, insect cells, and animal cells, can be used as long as they can express human CD48. As the expression vector, arbitrary expression vectors can be used as long as they have an appropriate promoter that can transcribe the DNA coding for CD48, in the host cell. The introduction of the recombinant vector into the host can be performed by a method selected as appropriate from known methods such as an electroporation method, a calcium phosphate method, and a lipofection method.

The obtained transformant is cultivated in an appropriate medium to express human CD48, and the human CD48 can be collected and obtained. As an immunogen for producing the antibody to human CD48, other than human CD48, a transformed cell expressing human CD48 may be used without any change, or may be isolated/purified as necessary and used.

Further, human CD48 can be produced using a chemical synthesis method such as a tBoc method (t-butyloxy carbonyl method) or an Fmoc method (fluorenyl methyloxy carbonyl method).

(2) Immunization with Human CD48

Animals are immunized with the human CD48 obtained as described above as an antigen, and antibody-producing cells are taken from spleen or lymph node. The kind of the immunized animals is not particularly limited, and, for example, can be selected as appropriate from mouse, rat, hamster, rabbit, goat, monkey, pig, horse, etc. The immunization can be performed by subcutaneously, intravenously, or intraperitoneally administrating the human CD48 antigen to the animals. An appropriate adjuvant may be added with the antigen to boost immunoresponsiveness of the immunized animals to the antigen. Normally, after the first administration of the antigen, the immunization is performed 2 to 5 times at intervals of 4 days to 2 weeks. A blood sample is collected from fundus venous plexus on Days 3 to 7 after each administration of the antigen, and its blood serum is used to measure reactivity with human CD48. A test animal exhibiting a sufficient antibody titer can be used as a supply source of antibody-producing cells.

The anti-human CD48 monoclonal antibody can be obtained by fusing antibody-producing cells and myeloma cells to create hybridomas, and cultivating the hybridomas. The antibody-producing cells can be obtained from the spleen of an animal that is confirmed to exhibit a sufficient antibody titer. The origin of the myeloma cells is not particularly limited, but the same kind of animal as the test animal is preferably used. For example, when a mouse is used as an immunized animal and antibody-producing cells are obtained, a mouse-derived cell line (e.g., a myeloma cell line derived from BALB/c mouse) is preferably used.

(3) Cell Fusion

Cell fusion can be performed using a known method such as a method using polyethylene glycol (a PEG method), a method using Sendai virus, or a method using an electrofusion device. When the PEG method is used, antibody-producing cells and bone marrow cells are mixed in an appropriate medium or buffer containing about 30 to 60% of PEG (average molecular weight 1000 to 6000), such that antibody-producing cell:myeloma cell=5 to 10:1, and are reacted with each other under the conditions of about 25 to 37° C. and pH6 to 8 for about 30 seconds to 3 minutes, whereby the antibody-producing cells and the bone marrow cells can be fused.

Selection of hybridoma can be performed by cultivating the fused cells in a selection medium. The selection medium is not particularly limited as long as it is a medium in which the parent cell line is killed and only the fused cells can proliferate. Normally, a hypoxanthine-aminopterin-thymidine medium (HAT medium) is used. After the cell fusion reaction ends, the cells are washed, and the PEG solution is removed. Then, in the selection medium cultivation, cultivation is performed while repeating medium replacement every 2 or 3 days, whereby selection of hybridoma is possible.

At the end, for the selected hybridoma, the affinity to human CD48 is measured by the following method, and an anti-human CD48 monoclonal antibody can be obtained.

(4) Measurement of Affinity to Human CD48

The affinity of the monoclonal antibody and its fragment to CD48 can be measured by any method known in the technical field. For example, the affinity can be measured by the following method. First, two types of cells, cells in which human CD48 is expressed and cells in which human CD48 is not expressed, are prepared. These two types of cells are the same except for presence/absence of expression of human CD48. Next, a fluorescence-labeled test antibody or its fragment is provided to each cell, and presence/absence of binding between the cells and the antibody or its fragment is measured using flow cytometry. An antibody that binds only to cells expressing human CD48 has specific affinity to human CD48, and an antibody that does not bind only to cells expressing human CD48 is an antibody having no or low specific affinity to human CD48. Further, the degree of the affinity of the monoclonal antibody to CD48 can be measured by the strength of a fluorescent signal detected by flow cytometry.

Other than the method using flow cytometry, an immunoassay can also be used to measure the affinity. In this case, a microtiter plate is coated with purified human CD48, and a test antibody or its fragment is added as a first antibody to each well to cause a reaction. Next, an antibody (second antibody) that can recognize the first antibody and that is labeled with an enzyme, a fluorescent substance, a luminous substance, a radioactive substance, or biotin is added to react with the first antibody. Then, the affinity of the test antibody or its fragment to human CD48 can be measured using the label of the second antibody as an indicator.

(5) In Light of Reducing Antigenicity to Human, the Human CD48 Monoclonal Antibody is Preferably a Humanized Antibody.

The humanized antibody (humanized anti-human CD48 monoclonal antibody) can be created according to any method known in the technical field. For example, first, a hybridoma producing a monoclonal antibody to human CD48 is created using non-human animal cells. Next, a DNA fragment coding for the amino acid sequences of the heavy and light chain variable regions (or super variable regions) of a non-human animal antibody that is produced from the hybridoma is obtained. This fragment is bound to a DNA coding for the amino acid sequence of a portion of a human-derived antibody other than the variable region (or super variable region), to create a DNA coding for a humanized antibody. At the end, the DNA is expressed in animal cells using an appropriate animal cell expression vector, to obtain the humanized antibody.

More particularly, a cDNA fragment coding for a heavy chain variable region comprising the amino acid sequence shown in SEQ ID NO: 1 and a cDNA fragment coding for a light chain variable region comprising the amino acid sequence shown in SEQ ID NO: 3 are inserted into a chimeric antibody production vector (e.g., an expression vector described in Reff M E et. al. Blood 83 435-445, 1994), and the vector is transfected into CHO cells to express the cDNAs, whereby an anti-human CD48 chimerized antibody can be produced. A particular example of the amino acid sequences of the H chain constant region and the L chain constant region of a specific human IgH gamma 1 antibody that can be used for such humanization is shown below.

The amino acid sequence of the H chain constant region of the human IgH gamma 1 antibody:

(SEQ ID NO: 7)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLEPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

The amino acid sequence of the L chain constant region of the human IgH gamma 1 antibody:

(SEQ ID NO: 8)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

A humanized antibody having lower antigenicity can be produced by substituting, with human-derived sequences, all the portions other than the super variable regions (CDR1, 2, and 3) in addition to the constant regions.

(6) Method for Obtaining Fragment of Anti-Human CD48 Monoclonal Antibody

As the anti-human CD48 monoclonal antibody, its fragment may be used as long as it has affinity to human CD48. Examples of the fragment of the anti-human CD48 monoclonal antibody include Fab, Fab', F(ab')$_2$, and scFv.

The Fab fragment is a fragment in which the L chain and the H chain are bound to each other via a disulfide bond, among fragments obtained by treating the antibody molecule with a protease papain. Thus, the Fab fragment of the anti-human CD48 monoclonal antibody can be obtained by treating the anti-human CD48 monoclonal antibody with papain, or can be obtained by inserting a DNA coding for the Fab fragment of the anti-human CD48 monoclonal antibody into an arbitrary expression vector and expressing the DNA in an appropriate host cell.

The F(ab')$_2$ fragment is a fragment that is obtained by treating the antibody molecule with a protease pepsin and in which two Fab fragments are bound to each other via a disulfide bond in a hinge region, and maintains affinity to the antigen. Thus, the F(ab')$_2$ fragment of the anti-human CD48 monoclonal antibody can be obtained by treating the anti-human CD48 monoclonal antibody with pepsin.

The Fab' fragment is a fragment that is obtained by cutting the disulfide bond in the hinge region of the above F(ab')$_2$ fragment and in which a full-length light chain and a heavy chain from the N terminal to the hinge region are bound to each other via a disulfide bond, and maintains affinity to the antigen. Thus, the Fab' fragment of the anti-human CD48 monoclonal antibody can be obtained by treating the above F(ab')$_2$ fragment, for example, with a reducing agent such as dithiothreitol to cut the disulfide bond in the hinge region. In addition, the Fab' fragment of the anti-human CD48 monoclonal antibody can also be obtained by inserting a DNA coding for the Fab' fragment into an arbitrary expression vector and expressing the DNA in an appropriate host cell.

The scFv fragment is a fragment in which the variable regions of the light chain and the heavy chain are bound to each other using a peptide linker and that maintains affinity to the antigen. Thus, the scFab' fragment of the anti-human CD48 monoclonal antibody can be obtained by constructing a DNA coding for the scFv fragment from a cDNA coding for the anti-human CD48 monoclonal antibody such that the length of a linker is preferably equal to or less than 8 amino acids, inserting the DNA into an arbitrary expression vector, and expressing the DNA in an appropriate host cell.

The anti-human CD48 monoclonal antibody obtained as described above can recognize myeloma stem cells, myeloma precursor cells, and myeloma plasma cells. Here, if the anti-human CD48 monoclonal antibody can have cellular cytotoxicity in addition to this recognition ability, the anti-human CD48 monoclonal antibody can kill and/or inhibit proliferation of myeloma stem cells, myeloma precursor cells, and myeloma plasma cells, and can be used effectively as an active ingredient of a therapeutic agent for diseases in which neoplastic proliferation of plasma cells occurs, such as myeloma.

Such a combination of cell recognition ability and cellular cytotoxicity is possible by (1) using an anti-human CD48 monoclonal antibody itself having cellular cytotoxicity or (2) binding another substance having cellular cytotoxicity to an anti-human CD48 monoclonal antibody. Hereinafter, each embodiment will be described.

I-II. Therapeutic Agent Containing Anti-Human CD48 Monoclonal Antibody Having Cellular Cytotoxicity In one embodiment, the present invention is a therapeutic agent, for diseases in which neoplastic proliferation of plasma cells occurs, which contains, as an active ingredient, a monoclonal antibody that is an antibody to the human CD48 and that has cellular cytotoxicity (hereinafter, also referred to as "anti-human CD48 cellular cytotoxicity monoclonal antibody").

I-II-I. Anti-Human CD48 Cellular Cytotoxicity Monoclonal Antibody

The anti-human CD48 cellular cytotoxicity monoclonal antibody is an antibody that is the aforementioned anti-human CD48 monoclonal antibody and that has cellular cytotoxicity. Here, the "cellular cytotoxicity" means a property of being able to kill and/or inhibit proliferation of myeloma stem cells, myeloma precursor cells, and myeloma plasma cells. Thus, as long as such an effect is provided, its action and mechanism are not particularly limited. For example, this activity is provided by one or a combination of two or more of complement-dependent cytotoxicity (CDC), antibody-dependent cellular cytotoxicity (ADCC), apoptosis induction, inhibition of a survival signal by blocking of ligand binding, and the like.

The anti-human CD48 cellular cytotoxicity monoclonal antibody intended by the present invention includes various antibodies, as long as they have cellular cytotoxicity and affinity to CD48. For example, it may be a modified antibody such as a humanized antibody, or may be its fragment (e.g., Fab, Fab', F(ab')$_2$, scFv, etc.). A preferable anti-human CD48 cellular cytotoxicity monoclonal antibody is, for example, a monoclonal antibody that has the amino acid sequence shown in SEQ ID NO: 1 as the amino acid sequence of a heavy chain variable region, the amino acid sequence shown in SEQ ID NO: 3 as the amino acid sequence of a light chain variable region, the amino acid sequence shown in SEQ ID NO: 5 as the amino acid sequence of a heavy chain constant region, and has the amino acid sequence shown in SEQ ID NO: 6 as the amino acid sequence of a light chain constant region. Other preferable monoclonal antibodies are antibodies that recognize the same epitope as the 1B4 monoclonal antibody, particularly monoclonal antibodies that can bind to the same epitope as this antibody, and more particularly the monoclonal antibodies described in the above I-I.

Whether or not an antibody has cellular cytotoxicity can be measured according to a known method. For example, complement-dependent cytotoxicity or antibody-dependent cellular cytotoxicity can be measured by the following method.

I-II-II. Method for Measuring Complement-Dependent Cytotoxicity (CDC)

Complement-dependent cytotoxicity can be measured according to a method of Brunner K. T., et al. (Brunner, K. T., et al., Immunology, 1968. 14:181-96). For example, myeloma cells that are target cells are cultivated in a RPMI1640 medium in which 10% FCS is added, and are prepared such that the number of cells is $0.5 \times 10^4$ to $1.0 \times 10^4$. An appropriate amount of Na$_2$$^{51}$CrO$_4$ is added thereto, a reaction is allowed to proceed at 37° C. for one hour, and the cells are labeled with $^{51}$Cr and washed to give target cells. A test antibody or isotype antibody, which is control, suspended in a fetal calf serum-added RPMI1640 medium is added to a 96-well plate such that the final concentration is 0.5 to 50 μg/mL, and then the target cells and a complement are added, and a reaction is allowed to proceed for 1.5 hours. The reaction solution is centrifuged, $^{51}$Cr released to the supernatant is measured with a γ-counter. The CDC activity can be obtained on the basis of the following equation.

CDC activity={([$^{51}$Cr release from cells used in experiment]−[voluntary $^{51}$Cr release in state where there is no antibody]/([maximum $^{51}$Cr release amount by addition of 1% Triton X-100]− [voluntary $^{51}$Cr release in state where there is no antibody])}×100

I-II-III. Method for Measuring Antibody-Dependent Cellular Cytotoxicity (ADCC)

Antibody-dependent cellular cytotoxicity can be measured according to a method of Brunner K. T., et al. (Brunner, K. T., et al., Immunology, 1968. 14:181-96). For example, as target cells, the same $^{51}$Cr-labeled myeloma-related cells as in the above case of the measurement of complement-dependent cytotoxicity can be used. As effector cells, SCID mouse bone marrow cells that are cultivated for six days in RPMI1640 in which 10% FBS, 10 ng/ml of mouse GM-CSF, and 40 IU/ml of human IL2 are added, or the like can be used. An antibody or its isotype antibody that is control is added to a 96-well plate such that the final concentration is 0.05 to 10 μg/mL, and the target cells ($1.0 \times 10^4$ cells) and the effector cells ($5 \times 10^5$ cells) are further added. A reaction is allowed to proceed at 37° C. for four hours, centrifugation is performed, and then $^{51}$Cr released to the supernatant is measured with a γ-counter. The ADCC activity can be obtained on the basis of the following equation.

ADCC activity={([$^{51}$Cr release from cells used in experiment]−[voluntary $^{51}$Cr release in state where there is no antibody]/([maximum $^{51}$Cr release amount by addition of 1% Triton X-100]−[voluntary $^{51}$Cr release in state where there is no antibody])}×100

The antibody, to human CD48, having cellular cytotoxicity can be obtained by producing anti-human CD48 monoclonal antibodies, assessing presence/absence of cellular cytotoxicity using the above method, and selecting an antibody having this activity.

The anti-human CD48 cellular cytotoxicity monoclonal antibody can bind specifically to myeloma stem cells, myeloma precursor cells, and myeloma plasma cells and can kill and/or inhibit proliferation of myeloma stem cells, myeloma precursor cells, and myeloma plasma cells, and thus is useful as an active ingredient of a therapeutic agent, particularly a radical therapeutic agent, for diseases in which neoplastic proliferation of plasma cells occurs, such as multiple myeloma.

The therapeutic agent of the present invention in the present embodiment may contain only the anti-human CD48 cellular cytotoxicity monoclonal antibody as an active ingredient, but may further contain, as necessary, pharmaceutically acceptable one or more additives, for example, one or more of a diluent, a preservative, a solubilizer, an emulsifier, an adjuvant, an antioxidant, an isotonizing agent, an excipient, and a carrier. In addition, the therapeutic agent may be a mixture with another antibody or another agent such as an antibiotic. Suitable carriers include, but are not limited to, a physiological saline, a phosphate buffered saline, a phosphate buffered saline glucose solution, and a buffered saline solution. Further, stabilizing agents such as amino acids, sugars, and surfactants, and inhibitors for adsorption to surface, which are known in this field, may be contained. As the form of a formulation, formulations including a lyophilized formulation (in this case, the formulation can be reconstructed and used by adding the above buffered solution), a slow release formulation, an enteric coated formulation, an injection, and drops are selectable according to aim of therapy and therapy planning.

As a route of administration of the therapeutic agent of the present invention, any of oral administration and parenteral administration (e.g., intraoral, tracheobronchial, rectal, subcutaneous, intramuscular, and intravenous) may be used, as long as the therapeutic effect for diseases in which neoplastic proliferation of plasma cells occurs is provided. Since the active ingredient contains the antibody, parenteral administration is preferred, and intravenous administration is further preferred. Thus, a preferable administration form is an injection. The injection is prepared using a carrier consisting of a salt solution, a glucose solution, or a mixture thereof, or the like.

Dosages and the number of times of administration of the therapeutic agent of the present invention depend on an intended therapeutic effect, an administration method, therapy duration, age, body weight, and the like, but the therapeutic agent can be administered to an adult patient afflicted with multiple myeloma, normally in an amount of 50 μg to 0.5 mg/kg per day.

I-III. Therapeutic Agent Containing One in which a Substance Having Cellular Cytotoxicity is Bound to Anti-Human CD48 Monoclonal Antibody In one embodiment, the present invention is a therapeutic agent, for diseases in which neoplastic proliferation of plasma cells occurs, which contains, as an active ingredient, one in which a substance having cellular cytotoxicity is bound to an anti-human CD48 monoclonal antibody.

The active ingredient of the therapeutic agent in the present embodiment is one in which a substance having cellular cytotoxicity is bound to an anti-human CD48 monoclonal antibody. As described above, the anti-human CD48 monoclonal antibody specifically recognize myeloma stem cells, myeloma precursor cells, and myeloma plasma cells. Thus, by binding the substance having cellular cytotoxicity to the anti-human CD48 monoclonal antibody, the substance can be transferred to myeloma stem cells, myeloma precursor cells, and myeloma plasma cells and caused to act specifically on these cells. In other words, by binding the substance having cellular cytotoxicity to the anti-human CD48 monoclonal antibody, the substance can be prevented from nonspecifically acting. Therefore, by the present invention, it is possible to treat diseases in which neoplastic proliferation of plasma cells occurs, such as multiple myeloma, while avoiding side effects caused by nonspecific action of the substance having cellular cytotoxicity on cells other than the above cells.

The anti-human CD48 monoclonal antibody used in the present embodiment is not particularly limited as long as it has affinity to human CD48, and includes the aforementioned various monoclonal antibodies (e.g., a modified antibody such as humanized antibody, and its fragment). Due to the nature of the invention, the anti-human CD48 monoclonal antibody does not have to itself have cellular cytotoxicity, but may be a monoclonal antibody having cellular cytotoxicity.

I-III-I. Substance Having Cellular Cytotoxicity

The substance having cellular cytotoxicity is a substance having a property of, when being bound to the anti-human CD48 monoclonal antibody and transferred to myeloma stem cells, myeloma precursor cells, and myeloma cells, being able to kill and/or inhibit proliferation of these cells. Since targeting and transferring to myeloma cells, myeloma precursor cells, and myeloma plasma cells are performed by the antibody, the substance having cellular cytotoxicity may not be one itself acting specifically on myeloma stem cells, myeloma precursor cells, and myeloma cells, as long as it has cellular cytotoxicity. Here, cellular cytotoxicity means a property of being able to kill and/or inhibit proliferation of cells. As long as such an effect is provided, its mechanism is not particularly limited, and an arbitrary substance can be used, but typical substances having cellular cytotoxicity are compounds known as anticancer agents. Particular examples include alkylating agents such as cyclophosphamide hydrate, ifosfamide, thiotepa, busulfan, merphalan, nimustine hydrochloride, ranimustine, dacarbazine, and temozolomide; antimetabolites such as methotrexate, pemetrexed sodium hydrate, fluorouracil, doxifluridine, capecitabine, tegafur, cytarabine, gemcitabine hydrochloride, fludarabine phosphate, nelarabine, cladribine, and levofolinate calcium; antibiotics such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin;

microtubule inhibitors such as vincristine sulfate, vinblastine sulfate, vindesine sulfate, and paclitaxel; aromatase inhibitors such as anastrozole, exemestane, letrozole, and fadrozole hydrochloride hydrate; platinum agents such as cisplatin, carboplatin, nedaplatin, and oxaliplatin; topoisomerase inhibitors such as irinotecan hydrochloride hydrate, nogitecan hydrochloride, etoposide, and sobuzoxane; adrenocorticosteroids such as prednisolone and dexamethasone; thalidomide and lenalidomide that is its derivative, and bortezomib that is a protease inhibitor. Among them, calicheamicin, merphalan, vincristine sulfate, doxorubicin hydrochloride, prednisolone, dexamethasone, thalidomide, lenalidomide, and bortezomib are preferred, and calicheamicin, which has produced good results in binding to an antibody, is more preferred. Any of the above-exemplified substances having cellular cytotoxicity are commercially available. As the substance having cellular cytotoxicity, one or more substances can be selected, bound to the anti-human CD48 monoclonal antibody, and used.

Alternatively, a radioisotope such as 90-Ittrium can be bound to the anti-human CD48 monoclonal antibody and used.

I-III-II. Method for Binding Substance Having Cellular Cytotoxicity and Antibody The substance having cellular cytotoxicity and the anti-human CD48 monoclonal antibody can be bound to each other by any method known in the technical field, as long as the cellular cytotoxicity of the substance and the affinity of the antibody to CD48 are not impaired. The substance and the antibody may be directly bound to each other or may be indirectly bound to each other via a linker or the like. The binding may be either a covalent bond or a noncovalent bond (e.g., ionic bond). For example, a reactive group (e.g., an amino group, a carboxyl group, a hydroxyl group, etc.) or a coordinating group in the antibody molecule is used to make the antibody contact with a cellular cytotoxicity substance having a functional group (in the case of a bacterial toxin or a chemotherapeutic agent) that can react with the reactive group to form a bond or having an ionic group (in the case of a radionuclide) that can form a complex with the coordinating group, whereby the antibody and the cellular cytotoxicity substance can be bound to each other. In addition, it is also possible to use biotin and avidin when forming a composite body. When the cellular cytotoxicity substance is a protein or peptide, a fusion protein of the antibody and the protein or peptide can be produced by a genetic engineering technique. In light of maintaining the affinity of the antibody, for example, the antibody and the substance having cellular cytotoxicity are preferably bound to each other via an amino acid present in an Fc fragment.

By binding the substance having cellular cytotoxicity to the anti-human CD48 antibody as described above, the active ingredient of the therapeutic agent of the present invention is obtained. The therapeutic agent of the present invention may be composed of only the cellular cytotoxicity substance and the anti-human CD48 antibody, but may contain one or more pharmaceutically acceptable additives as necessary. As additives, those described in the above I-II. can be used. In addition, the therapeutic agent of the present invention may be a mixture with another antibody or another agent such as an antibiotic. As a carrier and the like, those described in the above I-II. can be used. As the form of a formulation, formulations including a lyophilized formulation (in this case, the formulation can be reconstructed and used by adding the above buffered solution), a slow release formulation, an enteric coated formulation, an injection, and drops are selectable according to aim of therapy and therapy planning.

As a route of administration of the therapeutic agent of the present invention, any of oral administration and parenteral administration (e.g., intraoral, tracheobronchial, rectal, subcutaneous, intramuscular, and intravenous) may be used, as long as the therapeutic effect for diseases in which neoplastic proliferation of plasma cells occurs is provided. Since the active ingredient contains the antibody, parenteral administration is preferred, and intravenous administration is further preferred. Thus, a preferable administration form is an injection. The injection is prepared using a carrier consisting of a salt solution, a glucose solution, or a mixture thereof, or the like. Dosages and the number of times of administration of the therapeutic agent of the present invention depend on an intended therapeutic effect, an administration method, therapy duration, age, body weight, and the like, but the therapeutic agent can be administered to an adult patient afflicted with a disease in which neoplastic proliferation of plasma cells occurs, for example, in an amount of 1 to 9 mg/m$^2$ body surface area per day.

II. Method for Screening Active Ingredient of Therapeutic Agent for Diseases in which Neoplastic Proliferation of Plasma Cells Occurs In one embodiment, the present invention is a method, for screening an active ingredient of a therapeutic agent for diseases in which neoplastic proliferation of plasma cells occurs, which includes (1) a process of sorting a substance that binds specifically to human CD48 and (2) a process of sorting a substance having cellular cytotoxicity. The substance searched for and obtained by the method of the present invention can bind specifically to human CD48 and has cellular cytotoxicity. Therefore, it is expected that when being administered to patients afflicted with diseases in which neoplastic proliferation of plasma cells occurs such as multiple myeloma, the substance specifically recognizes myeloma stem cells, myeloma precursor cells, and myeloma plasma cells and exerts cytotoxic effects thereon, whereby diseases in which neoplastic proliferation of plasma cells occurs can be treated.

The substance to be screened by the present invention is not particularly limited as long as it is one sorted by the processes (1) and (2), and is preferably an antibody.

The process (1) is a process of sorting a substance that specifically recognizes and binds to human CD48, and can be performed according to the methods described in (4) in the above "Method for producing anti-human CD48 monoclonal antibody", but is not limited thereto.

Hereinafter, a particular method is exemplified. Two types of cells, cells in which human CD48 is expressed and cells in which human CD48 is not expressed, are prepared. These two types of cells are the same except for presence/absence of expression of human CD48. Next, a fluorescence-labeled test substance is provided to each cell, and presence/absence of binding between the cells and the substance is measured using flow cytometry. A substance that binds only to cells expressing human CD48 has specific affinity to human CD48, and an antibody that does not bind only to cells in which human CD48 is expressed is an antibody having no or low specific affinity to human CD48. The degree of the affinity of the antibody to CD48 can be measured by the strength of a fluorescent signal detected by flow cytometry.

Other than the method using flow cytometry, an immunoassay can also be used to measure the affinity. In this case, a microtiter plate is coated with purified human CD48, and a test substance is added to each well to cause a reaction. Next, an antibody that can recognize the substance and that is labeled with an enzyme, a fluorescent substance, a luminous substance, a radioactive substance, or biotin is added to react with the substance. Then, the affinity of the test substance to human CD48 can be measured using the label of the antibody as an indicator.

The test substance is not particularly limited as long as the affinity to human CD48 can be measured by these methods, but is preferably an antibody.

The process (2) is a process of sorting a substance having cellular cytotoxicity, and the cellular cytotoxicity can be measured using the methods described in the above and for measuring complement-dependent cytotoxicity (CDC) and for measuring antibody-dependent cellular cytotoxicity (ADCC).

The candidate substances sorted as described above can further be sorted out as a more practical active ingredient of a therapeutic agent for multiple myeloma, by further conducting a drug effect test, a stability test, etc. using sick nonhuman animals with diseases in which neoplastic proliferation of plasma cells occurs.

III. Method for Identifying Neoplastic Plasma Cells

In one embodiment, the present invention is a method for identifying neoplastic plasma cells, including a process of causing an anti-human CD 48 monoclonal antibody to act on a sample taken from a patient afflicted with a disease in which neoplastic proliferation of plasma cells occurs. As described above, the anti-human CD48 monoclonal antibody is an antibody that binds specifically to human CD48 to specifically recognize myeloma stem cells, myeloma precursor cells, and myeloma plasma cells. Thus, the anti-human CD48 monoclonal antibody is caused to act on the sample containing neoplastic plasma cells, and an antibody that binds to cells expressing CD48 is detected, whereby it is possible to identify the neoplastic plasma cells in the sample. Here, the sample is a sample (e.g., bone marrow, blood, tumor, etc.) that is taken from a patient afflicted with a disease in which neoplastic proliferation of plasma cells occurs and that contains neoplastic plasma cells, is preferably body fluid, and is further preferably blood. In order to facilitate detection, the anti-human CD48 monoclonal antibody may be modified with a fluorescent dye or radioisotope. The identification of myeloma plasma cells may be performed using the anti-human CD48 monoclonal antibody alone or in combination with another antibody (e.g., an anti-human CD38 monoclonal antibody). For example, a sample taken from the bone marrow of a myeloma patient is co-stained with the fluorescence-labeled anti-human CD48 monoclonal antibody and the anti-human CD38 monoclonal antibody, and cells in the sample are separated for CD38 and CD48 by flow cytometry, whereby the myeloma cell population can easily be identified. When these monoclonal antibodies are used, the myeloma plasma cells can be identified as cells that have strong positivity for CD38 and CD48 (e.g., see Example 9).

IV. Reagent or Kit for Monitoring Progression of or Therapeutic Effect for Diseases in which Neoplastic Proliferation of Plasma Cells Occurs In one embodiment, the present invention relates to a reagent or kit, for monitoring progression of or a therapeutic effect for diseases in which neoplastic proliferation of plasma cells occurs, including a monoclonal antibody to human CD48. As described above, the anti-human CD48 monoclonal antibody can specifically recognize myeloma stem cells, myeloma precursor cells, and myeloma plasma cells, and hence these cells can be identified. Thus, for a patient afflicted with a disease in which neoplastic proliferation of plasma cells occurs, for example, the concentrations (numbers) of myeloma stem cells, myeloma precursor cells, and myeloma plasma cells in blood can be measured using the anti-human CD48 monoclonal antibody, to monitor the progression of or the therapeutic effect for the disease. The monitoring reagent of the present invention may include only the anti-human CD48 monoclonal antibody, and may additionally include an arbitrary component required for monitoring, as necessary. The monitoring kit of the present invention may include, in addition to the anti-human CD48 monoclonal antibody, another component (e.g., another antibody, a buffer, a fluorescent dye, etc.), an instrument, a manual, and the like. When monitoring is performed according to the present invention, it can be used for determination of therapy planning.

EXAMPLES

Test Method: Flow Cytometry and Sorting

In the following examples, flow cytometry sorting used for sorting cells were performed as follows. Bone marrow monocytes taken from the iliac bone of a myeloma patient from which informed consent was obtained were suspended in an ACK solution (150 mM $NH_4Cl$ and 10 mM $KHCO_3$) and allowed to stand for 3 minutes at 4° C. to remove red blood cells. After washing with a PBS (Phosphate-buffered saline) in which 2% fetal bovine serum was added, in order to prevent nonspecific binding of an antibody, blocking was performed in a PBS containing 10% human AB type serum, for 20 minutes at 4° C. Then, each antibody (see the following) labeled with a fluorescent dye was added to perform staining for 30 minutes at 4° C., and washing was performed with a PBS. Then, the bone marrow monocytes were suspended in a PBS containing 1 µg/ml of propidium iodide (PI) and subjected to flow cytometry analysis. Analysis and cell sorting were performed using a FACS Aria cell sorter (manufactured by Becton Dickinson Immunocytometry System).

For staining cells, the following monoclonal antibodies were selected and used as appropriate:
APC or Cy7PE-conjugated CD34 (manufactured by BD Pharmingen), Cy7PE or Cy7APC-conjugated CD19 (manufactured by BD pharmingen), FITC-conjugated CD38 (manufactured by eBiosciences), APC-conjugated CD38 (manufactured by BD pharmingen), PE-conjugated CD138 (manufactured by BD pharmingen), Biotin-conjugated CD3 (manufactured by BD pharmingen), Biotin-conjugated CD14 (manufactured by eBiosciences), Cy5PE-conjugated streptoavidin (manufactured by eBiosciences), Cy5PE-conjugated CD235 (manufactured by Biolegend), FITC-conjugated CD48 (manufactured by eBiosciences), and Cy7PE-conjugated mouse CD45 (manufactured by eBiosciences).

Example 1

Screening Target Molecules Suitable for Radical Therapy for Multiple Myeloma

For radical therapy for multiple myeloma, it is important to target myeloma stem cells and myeloma precursor cells that are at a stage prior to differentiation into myeloma plasma cells. Meanwhile, it is also important to exclude, from targets, hematopoietic stem cells required for producing normal B cells and plasma cells. In order to target myeloma stem cells and myeloma precursor cells while excluding hematopoietic stem cells from targets, it is desired to find a molecule that is not expressed in hematopoietic stem cells but is expressed in common on the cell surfaces of myeloma stem cells and myeloma precursor cells, and to use the molecule as an indicator for target cells. Thus, in order to find such a molecule, the following screening was performed.

First Screening

First, genes coding for molecules expressed in myeloma stem cells and myeloma precursor cells were identified using the following three methods (A) to (C).

(A) First Method: Identification of Genes Expressed in Myeloma Precursor Cells Using Signal Sequencing Trap Method Myeloma precursor cells (CD19$^-$CD38$^{++}$CD138$^-$ myeloma precursor cells) were obtained from a multiple myeloma patient, and genes coding for cell surface proteins were identified from among genes expressed in these cells.

First, myeloma precursor cells were separated from bone marrow cells derived from the multiple myeloma patient, by flow cytometry cell sorting. Total RNA was taken from the cells using a Trizol reagent (Invitrogen, Carlsbad, Calif.). Next, cDNA was created from all the RNAs using a PCR cDNA synthesis kit (SMART™: Clontech, Palo Alto, Calif.) and amplified by PCR to obtain a cDNA library. The cDNA of the library was cut by a restriction enzyme RsaI, and then a BstXI adaptor was bound thereto. Then, electrophoresis was performed on 1% agarose gel, cDNA having a size of 0.5 kb to 2.0 kb was cut out from the gel, purified, and then inserted into a pMX-SST vector (provided by Professor Toshio Kitamura of the Institute of Medical Science, the University of Tokyo). The SST-REX library created as described above was introduced into BaF3 cells according to a signal sequencing trap method described in a report of Kitamura et al. (Kojima, T. and T. Kitamura, A signal sequence trap based on a constitutively active cytokine receptor. Nat Biotechnol, 1999. 17(5): p. 487-90), and then screened to comprehensively separate cDNAs included in the cDNA library and coding for cell surface proteins. Gene analysis was conducted on the separated cDNAs to identify gene names from gene sequences. The identified genes are shown in the following Table 1 as genes expressed in myeloma precursor cells.

TABLE 1

Genes that were identified by the signal sequencing trap method, were highly expressed in myeloma precursor cells, and code for cell surface proteins.
Gene name Phosphatidylinositol glycan anchor biosynthesis, class B (PIGB)
Solute carrier family 25 (mitochondrial carrier; adenine nucleotide translocator), member 5 (SLC25A5)
Chromosome 2 open reading frame 28 (C2orf28), transcript variant 2
Niemann-Pick disease, type C2 (NPC2)
Interecellular adhesion molecule 2 (ICAM2), transcript (CD102)
Lysosomal-associated membrane protein 2 (LAMP2), transcript variant LAMP2B (CD107b)
SEL1L (Gene names registered in NCBI Genbank (http://www.ncbi.nlm.nih.gov/) are shown)

(B) Second Method: Identification of Genes Highly Expressed in Common in Myeloma Stem Cells and Myeloma Precursor Cells Using Gene Chip Myeloma stem cells (CD19$^+$ cells) and myeloma precursor cells (CD19$^-$CD38$^{++}$CD138$^-$ cells) were obtained from a multiple myeloma patient different from the patient from which the cells were obtained in the above first method, and genes expressed in these cells were identified.

Figure 2:
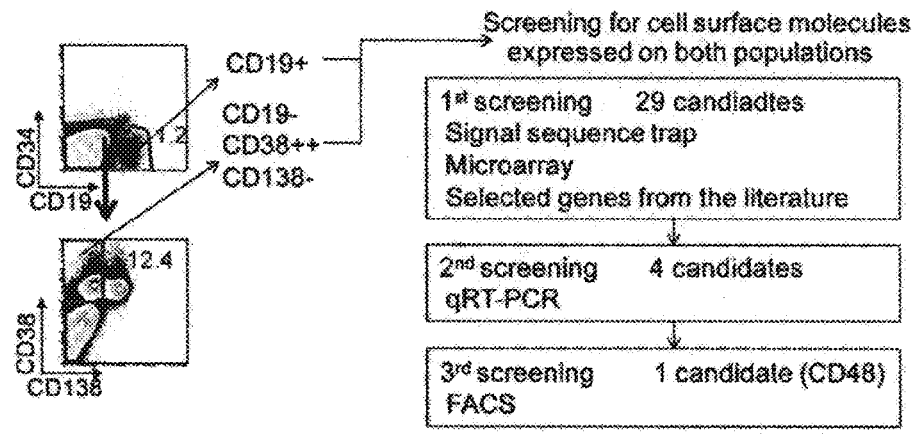
FIG. 2 illustrates a strategy of separation of myeloma stem cells and myeloma precursor cells by flow cytometry cell sorting and identification of cell surface molecules highly expressed on both cells.

Myeloma stem cells (CD19$^+$ cells) and myeloma precursor cells (CD19$^-$CD38$^{++}$CD138$^-$ cells) were separated from the bone marrow cells derived from the other myeloma patient, by flow cytometry sorting (see FIG. 2). Next, total RNA was taken from each of the separated cell fractions using a Micro RNeasy kit (manufactured by Qiagen). After cDNA was created from 20 ng of the total RNA using a GeneChip Two-Cycle cDNA Synthesis Kit (manufactured by Affymetrix), a 1$^{st}$ cycle cRNA was created using a MEGAscript® T7 Kit (manufactured by Ambion) and further a Biotinylated cRNA was created using an IVT Labeling Kit (manufactured by Affymetrix). After fragmentation was performed, 11.25 µg of cRNA was hybridized to GeneChip Human Genome U133 Plus 2.0 Array for 16 hours at 45° C. After the GeneChips were washed with Affymetrix Fluidics Station 450 and stained, the GeneChips were scanned using GeneChip Scanner 3000 7G. The result was obtained using Microarray Suite version 5.0 (MAS5.0), and global scaling was used as a standardization method. In this manner, molecules highly expressed in both myeloma stem cells and myeloma precursor cells are selected from among the identified genes. The selected genes are shown in Table 2.

TABLE 2

Genes that were highly expressed in both myeloma stem cells (CD19$^+$ myeloma stem cells) and myeloma precursor cells (CD19$^-$CD38$^{++}$CD138$^-$ myeloma precursor cells) and code for cell surface proteins.

| | Scale signal | |
|---|---|---|
| Gene name | Myeloma stem cell | Myeloma precursor cell |
| MMSC-2 | 12982.9 | 16945.6 |
| CDNA clone IMAGE: 6208446 | 8743.4 | 21087.6 |
| endotheline receptor type B | 7787.4 | 38147.1 |
| CD48 | 6653.5 | 15464.5 |
| intercellular adhesion molecule 3 | 6212 | 15605.8 |
| tumor necrosis factor receptor superfamily, member 17 | 5118.3 | 20796.3 |
| CD9 molecule | 4984 | 2819 |
| cDNA DKFZp586A0722 | 3464.2 | 7510.6 |
| Activated leukocyte cell adhesion molecule (CD166) | 1936.5 | 3276.8 |
| intercellular adhesion molecule 2 | 1415.1 | 1797.1 |
| G protein coupled receptor, family C, group 5, member D | 1210.7 | 8974.6 |
| chemokine (C-C motif) receptor 2 (CD192) | 1179.3 | 8470.8 |

(C) Third Method: Searching for Genes Coding for Candidate Molecules on the Basis of Literature Information Genes coding for proteins that can be targets for antibody therapy were selected from the molecules reported to be expressed in myeloma cells in a literature. In other words, genes that are not widely expressed in many organs and that are unclear to be expressed in a CD34 positive hematopoietic stem cell fraction in the released gene expression database Gene Card (see the website having a URL ending in genecards.org/) were selected from the cell surface molecules reported to be expressed in myeloma cells in a literature (e.g., Claudio, J. O., et al., Blood, 2002. 100:2175-86.) searchable in PubMED (see the website having a URL ending in ncbi.nlm.nih.gov/pubmed/). The selected genes are shown in Table 3.

TABLE 3

Gene name

NTRK1, CD36, CD28, CDld, CSF2R, SPAG4, CD56, MMSC-3, CD117, MMSC-4

Second Screening

Figure 3:
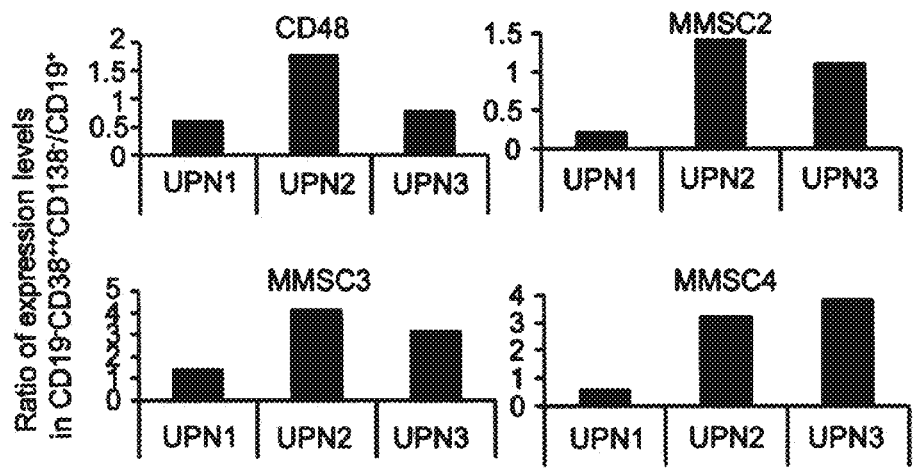
FIG. 3 shows expression ratios in mRNA level of a CD48 molecule and MMSC2 to MMSC4 molecules in myeloma stem cell fractions and myeloma precursor cell fractions.

Genes that were actually highly expressed in myeloma stem cells, myeloma precursor cell, and myeloma plasma cells that were derived from a plurality of patients were screened from among the candidate genes obtained by the above first screening. First, molecules (e.g., Niemann-Pick disease, type C2 (NPC2) and CD9 molecule) expected to be ubiquitously expressed in multiple organs from searching of the gene expression database were excluded from the candidate genes shown in the above Tables 1 to 3. A PCR primer was produced for each of the remaining genes. Meanwhile, myeloma stem cells (CD19⁺ cells) and myeloma precursor cells (CD19CD38⁺⁺CD138⁻ cells) were taken from three different myeloma patients, and cDNA was created similarly as in the first method (A). Quantitive PCR was performed using the primer created for each of the obtained candidate molecules. Quantitive RT-PCR was performed by an SYBR Green method using ABI 7700 real-time PCR machine (manufactured by Applied Biosystems). The expression level of each gene was standardized by the expression level of β-actin. When molecules having a low possibility of being expressed in a myeloma stem cell fraction (the difference in Ct value from β-actin is equal to or higher than 10) were excluded and then molecules observed to have the same expression level in a myeloma precursor cell fraction as in a myeloma stem cell fraction were selected, four molecules, CD48 and MMSC2 to MMSC4, were obtained (FIG. 3).

From the above results, it is confirmed that the CD48 and MMSC2 to MMSC4 molecules are expressed in common in the myeloma stem cell fraction and the myeloma precursor cell fraction, and the possibility is suggested that they can be ideal target molecules.

Example 2

Measurement of Expression Pattern of Each Molecule in Myeloma Stem Cells, Myeloma Precursor Cells, Myeloma Plasma Cells, and Hematopoietic Stem Cells Presence/absence of expression of CD48 and MMSC2 to MMSC4 on the cell surfaces of myeloma stem cells, myeloma precursor cells, myeloma plasma cells, and hematopoietic stem cells was measured using a commercially available anti-CD48 antibody (eBioscience) and antibodies to MMSC2 to MMSC4.

Bone marrow cells derived from a multiple myeloma patient were stained with APC-conjugated CD34 (manufactured by BD Pharmingen), Cy7APC-conjugated CD19 (manufactured by BD pharmingen), Cy7PE-conjugated CD38 (manufactured by eBiosciences), PE-conjugated CD138 (manufactured by BD pharmingen), Biotin-conjugated CD3 (manufactured by BD pharmingen), Biotin-conjugated CD14 (manufactured by eBiosciences), Cy5PE-conjugated CD235 (manufactured by Biolegend), and FITC-conjugated CD48 (manufactured by eBiosciences) (or FITC-conjugated MMSC2 to MMSC4), and washed. Then, second staining was performed with Cy5PE-conjugated streptoavidin (manufactured by eBiosciences). As an Isotype control, a sample in which FITC-conjugated mouse IgG was added instead of FITC-conjugated CD48 and MMSC2 to MMSC4 was prepared at the same time. These samples were analyzed using flow cytometry to measure expression distributions of the CD48 molecule and the MMSC2 to MMSC4 molecules in protein level in a CD19⁺ myeloma stem cell fraction, a CD19⁻CD38⁺⁺CD138⁻ myeloma precursor cell fraction, CD138⁺ mature myeloma plasma cell fraction, and a CD34⁺ hematopoietic stem/precursor cell fraction.

Figure 4:
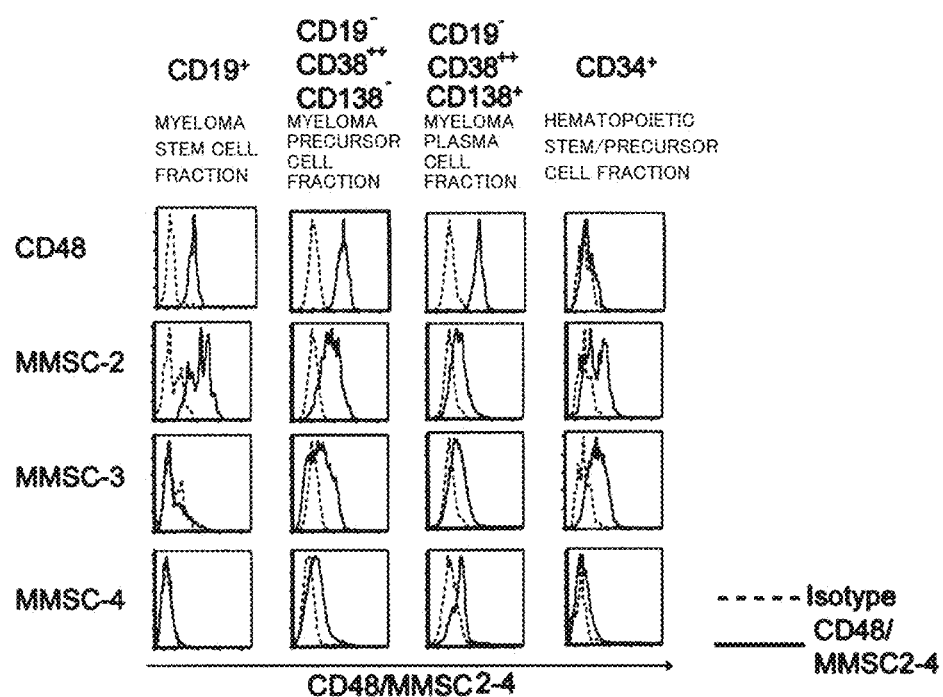
FIG. 4 shows a result of expression analysis in protein level of the CD48 molecules and MMSC2 to MMSC4 molecules in myeloma stem cell fractions, myeloma precursor cell fractions, myeloma plasma cell fractions, and hematopoietic stem/precursor cell fractions.

Screening was performed using specimens from myeloma patients of three cases. An example of the results is shown in FIG. 4. In each histogram shown in FIG. 4, the Y axis indicates the number of cells, and the X axis indicates the expression intensity of CD48 or MMSC2 to MMSC4. From the results shown in FIG. 4, it is confirmed that CD48 is expressed at a high level in any of the CD19⁺ myeloma stem cell fraction, the CD19⁻CD38⁺⁺CD138⁻ myeloma precursor cell fraction, and the CD138⁺ mature myeloma plasma cells, and has a low expression level in the CD34⁺ hematopoietic stem/precursor cell fraction. On the other hand, it is confirmed that the MMSC2 molecule is expressed at a relatively high level also in the CD34⁺ hematopoietic stem/precursor cell fraction. It is confirmed that the MMSC3 molecule and the MMSC4 molecule are not expressed or are expressed at a relatively low level in the CD19⁺ myeloma stem cell fraction and the CD19⁻CD38⁺⁺CD138⁻ myeloma precursor cell fraction. As a result, it is seen that only CD48 is expressed on the cell surfaces of all of the myeloma stem cells, the myeloma precursor cells, and the myeloma plasma cells, and has a sufficiently low expression level in the hematopoietic cells. Thus, it is strongly suggested that the CD48 molecule can be an ideal target molecule indicating cells to be targeted for therapy, in radical therapy for multiple myeloma. On the other hand, for MMSC2, since expression in the hematopoietic stem cells is observed, it is suggested that MMSC2 is not ideal as an indicator indicating target cells for therapy for multiple myeloma. In addition, for MMSC3 and MMSC4, since the expression levels on the cell surfaces of the myeloma stem cells and/or the myeloma precursor cells are low, it is suggested that MMSC3 and MMSC4 are not ideal as indicators indicating target cells for therapy for multiple myeloma.

Example 3

Figure 5:
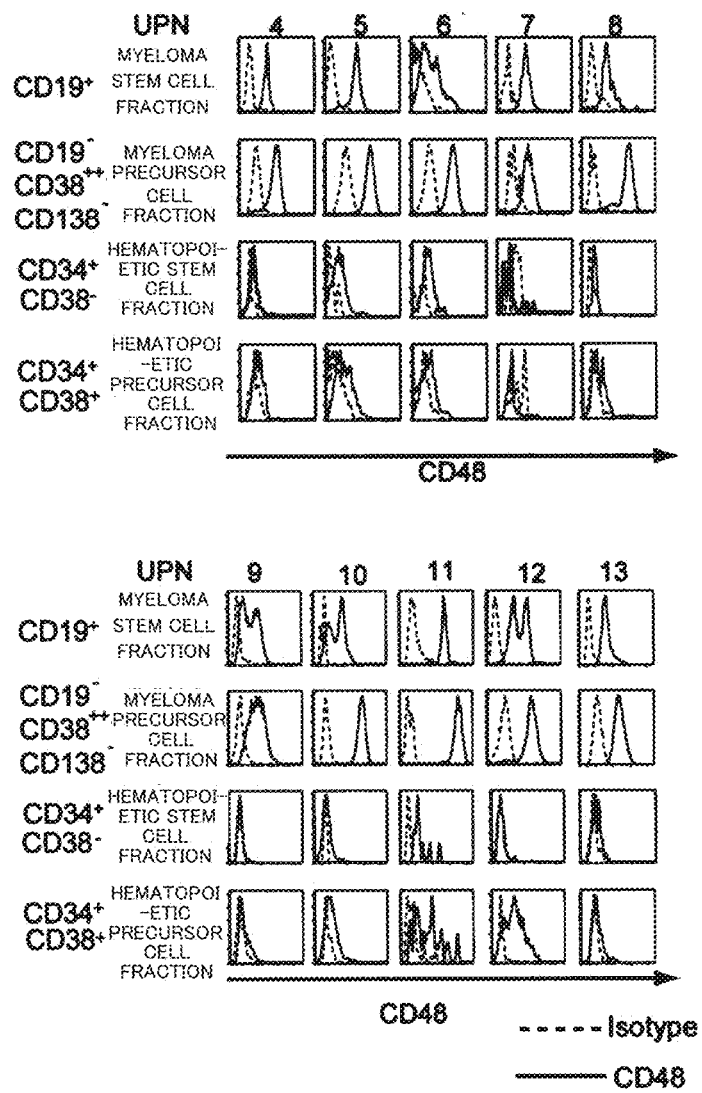
FIG. 5 shows expression patterns of the CD48 molecule in each of cell fractions (myeloma stem cell fractions, myeloma precursor cell fractions, hematopoietic stem cell fractions, and hematopoietic precursor cell fractions) derived from myeloma patients of 10 cases (UPN4 to 13).

Confirmation of Expression Distribution of CD48 Using Cells Derived from a Plurality of Patients In order to confirm whether the expression distribution of CD48 confirmed in Example 2 is the same as in cells derived from other patients, bone marrow cells were taken from a plurality of patients, and expression of CD48 in each cell fraction was measured similarly as in Example 2. The results of analysis of the bone marrow specimens from myeloma patients of 10 cases are shown in FIG. 5. From the results shown in FIG. 5, it becomes clear that the anti-CD48 antibody is bound to the cell fractions derived from the other patients, in the same pattern as in the results in Example 3. In other words, it is confirmed that the CD48 molecule is expressed at a high level in any of the myeloma stem cell fraction and the myeloma precursor cell fraction and has a low expression level in the hematopoietic stem cell fraction and the hematopoietic precursor cell fraction.

As described above, from the results in Examples 2 and 3, it is confirmed that CD48 is highly expressed on the cell surfaces of the myeloma stem cells, the myeloma precursor cells, and the myeloma plasma cells derived from multiple myeloma patients and is not expressed at all or is expressed at a very low expression level in the hematopoietic stem cells. Thus, since use of CD48 as an indicator makes it possible to target a series of cells from the CD19⁺ myeloma stem cell fraction to the CD19⁻CD38⁺⁺CD138⁻ myeloma precursor cell fraction and to exclude hematopoietic stem cells from targets, it is strongly suggested that CD48 is a molecule that becomes an ideal indicator for radical therapy for multiple myeloma.

Example 4

Creation of Monoclonal Antibody to CD48

In order to examine whether the CD48 molecule itself is appropriate as a target for radical therapy for multiple myeloma, a monoclonal antibody to CD48 was created. First, a human CD48 cDNA (FLJ clone, manufactured by Toyobo Co., Ltd.) was inserted into an MSCV-ires-GFP vector, and the vector was introduced into BaF3 cells using retrovirus to create human CD48-expressing mouse cells. The cells were immunized in Foot pad of a Balb/c mouse four times, then, the lymph node was taken out, and cell fusion was performed with mouse myeloma cells SP2/0 to produce hybridomas. The fused cells were cultivated in an HAT medium. Hybridomas selected on the basis of presence/absence of proliferation were cultivated on a microtiter plate, and binding to BaF3 cells in which CD48 was expressed was observed for the supernatant by flow cytometry to perform screening, to obtain CD48 antibody producing hybridomas. Through such a single cell fusion, hybridomas of 4 clones producing the anti-human CD48 monoclonal antibody were obtained. Among them, it was confirmed that two clones (1B4 and 2E2) are IgG2a subclass. Confirmation of the subclass was performed using an Isotyping kit (Roche).

Further, the base sequences and the amino acid sequences of the variable regions of antibody molecules produced by the hybridomas 1B4 and 2E2 were determined. The determination of the sequences was performed according to an already-reported method of Coloma et al. (Coloma M J et al. Journal of Immunological Methods 152, 89-104, 1992). In other words, cDNA fragments of the H chain and κ chain variable regions were amplified by a PCR reaction with, as a template, cDNA produced from RNA derived from each hybridoma, and the base sequences were decoded. The decoded amino acid sequence (SEQ ID NO: 1) and base sequence (SEQ ID NO: 2) of the κ chain variable region and super variable regions (CDR1 to 3) are shown in FIG. 6. The decoded amino acid sequence (SEQ ID NO: 3) and base sequence (SEQ ID NO: 4) of the L chain (κ chain) variable regions and super variable regions (CDR1 to 3) are shown in FIG. 7. In addition, since the sequence obtained from 1B4 completely coincides with the sequence derived from 2E2, it becomes clear that these two clones produce antibodies having exactly the same sequence.

Example 5

Measurement of Cellular Cytotoxicity of Anti-Human CD48 Monoclonal Antibody

Presence/absence of cellular cytotoxicity in vitro of the anti-human CD48 monoclonal antibody created in Example 4 was checked. In the test, for the monoclonal antibody produced by 1B4 that was confirmed to belong to IgG2a subclass, presence/absence of complement-dependent cytotoxicity (CDC) was checked using a chromium release method. A baby rabbit complement (Cedarene) was used as a complement. As myeloma cells, myeloma cell lines OPM2 and U266 were used. The OPM2 cell line and the U266 cell line highly express the CD48 molecule as shown in FIG. 8. Each myeloma cell line was labeled with $^{51}$Cr for two hours and washed three times. The labeled cells ($1\times10^4$ cells) were cultivated in 96-well U-bottomed plates ($1\times10^4$ cells) in 160 μL of RPMI1640+fetal bovine serum in which the anti-human CD48 monoclonal antibody or an isotype control (10 μg/ml in final) and 25% baby rabbit complement were added. After the cultivation under the conditions of 37° C. and 5% $CO_2$ for 90 minutes, $^{51}$Cr released to the supernatant was counted. Specific cellular cytotoxicity was calculated as follows.

CDC activity={([$^{51}$Cr release from cells used in experiment]−[voluntary$^{51}$Cr release in state where there is no antibody]/([maximum$^{51}$Cr release amount by addition of 1% Triton X-100]− [voluntary$^{51}$Cr release in state where there is no antibody])}×100

Figure 9:
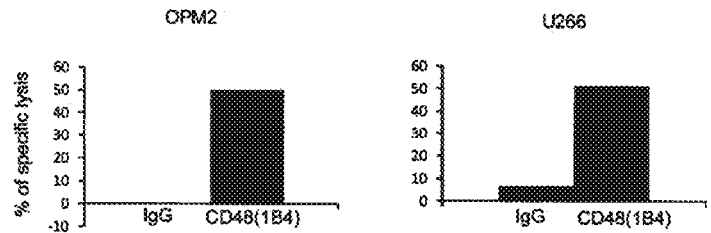
FIG. 9 shows complement-dependent cytotoxicity of the anti-human CD48 monoclonal antibody (1B4) to the myeloma cell lines OPM2 and U266.

The results of the measurement are shown in FIG. 9. As shown in FIG. 9, it is confirmed that the 1B4 monoclonal antibody clearly has cellular cytotoxicity to the myeloma cell lines OPM2 and U266. The results demonstrate that the 1B4 monoclonal antibody and the antibody that recognizes the same epitope as the 1B4 monoclonal antibody can be active ingredients for therapy for multiple myeloma and that checking of the therapeutic effect in vivo for multiple myeloma using these monoclonal antibodies makes it possible to check efficacy of treating multiple myeloma with, as a target, cells expressing CD48.

Example 6

In Vivo Myeloma Cell Proliferation Inhibition Effect of Anti-Human CD48 Cellular Cytotoxicity Monoclonal Antibody The therapeutic effect in vivo for multiple myeloma was checked using the anti-human CD48 monoclonal antibody confirmed to have cellular cytotoxicity in Example 5.

Figure 10:
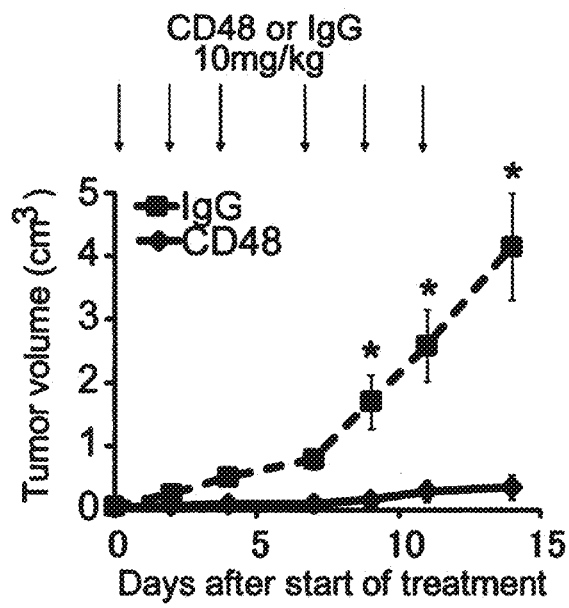
FIG. 10 shows the volume changes of tumor masses formed by a myeloma cell line subcutaneously transplanted in Rag2−/−cγ−/− mice (an anti-CD48 antibody administration group and a control IgG administration group).
Figure 11:
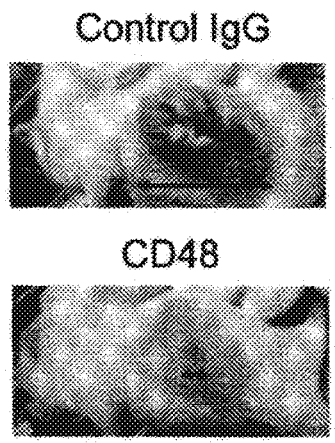
FIG. 11 shows the sizes of the tumor masses in the Rag2−/−cγ−/− mice (the anti-CD48 antibody administration group and the control IgG administration group) on Day 12, wherein the arrow indicates the width of the tumor.

Myeloma cell line OPM2 cells ($1\times10^7$ cells) were subcutaneously transplanted into Rag2$^{-/-}$cγ$^{-/-}$ mice irradiated with radiation of 2 Gy. When the tumor volume exceeded 10 mm$^3$ (10 days after the transplantation of the tumor), the mice were divided into a CD48 antibody administration group and a control IgG administration group, and 10 mg/kg of the anti-human CD48 monoclonal antibody (1B4) or control IgG was administered three times a week (every second days). Measurement of the tumor volume was performed three times a week (every second days), and the volume was represented by the following approximate value: long diameter×short diameter×height/2. The time when the volume of the tumor mass formed by the transplanted myeloma cell line OPM2 exceeded 10 mm$^3$ is set to Day 0, and the change of the tumor volume from that day is shown in FIG. 10. In addition, the sizes of the tumors in the control (IgG administration) mouse and the 1B4 antibody administration mouse on Day 12 are shown in FIG. 11. The arrow indicates the width of the tumor.

As shown in FIGS. 10 and 11, while the myeloma cells exponentially proliferated when control IgG was administered, proliferation of the myeloma cells was almost completely inhibited when the anti-human CD48 monoclonal antibody (1B4) having cellular cytotoxicity was administered.

Example 7

Therapeutic Effect of Anti-Human CD48 Cellular Cytotoxicity Monoclonal Antibody for Myeloma Cells Transplanted in Bone Marrow In order to check the effect for myeloma cells in a more physiological environment, the effect of antibody administration for myeloma cells transplanted in bone marrow was examined. After $3\times10^5$ myeloma cell line OPM2 cells were transplanted into the bone marrows of Rag2$^{-/-}$cγ$^{-/-}$ mice irradiated with radiation of 2 Gy, bone marrow aspiration was performed on Day 10, and the chimerism of human myeloma cells was analyzed on the basis of the frequency of hCD38-expressing cells. In addition, 5 mg/kg of the CD48 antibody or mouse IgG as control was intravenously administered on Day 11, Day 13, and Day 15. Then, in order to examine the effect of the antibody, the chimerism of human myeloma cells in bone marrow was analyzed again on Day 16.

Figure 12:
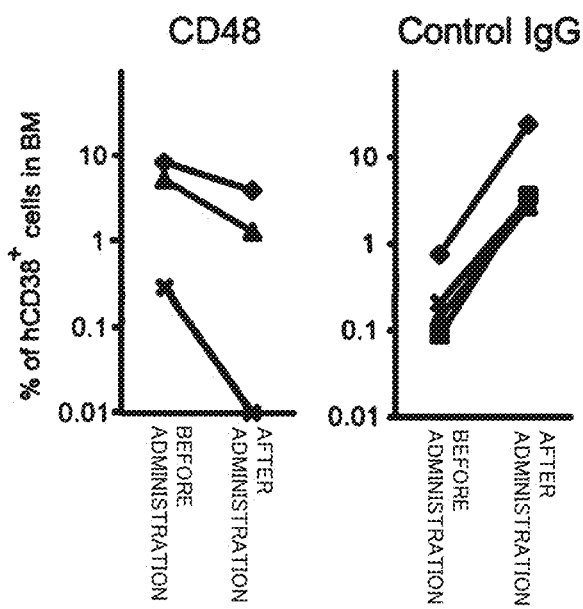
FIG. 12 shows changes of the chimerisms of myeloma cells in the Rag2−/−cγ−/− mice (the anti-CD48 antibody administration group and the control IgG administration group) before and after the administration of an anti-CD48 antibody or mouse IgG.

While increase in chimerism of myeloma cells was markedly observed in any of the mice of the control IgG antibody administration group, the chimerism of myeloma cells decreased for the CD48 antibody (FIG. 12). From these experimental results, it becomes clear that the anti-human CD48 monoclonal antibody (1B4) and the antibody that recognizes the same epitope as the anti-human CD48 monoclonal antibody have very high cellular cytotoxicity to myeloma cells expressing CD48. By targeting CD48, not only myeloma plasma cells but also myeloma stem cells and myeloma precursor cells can be targeted, and thus the possibility is strongly suggested that the anti-human CD48 monoclonal antibody is effective for radical therapy for multiple myeloma. Further, since specifically killing cells in which human CD48 is expressed, with human CD48 as an indicator, is effective for radical therapy for multiple myeloma, it is suggested that a combination of a substance (e.g., a monoclonal antibody) that specifically recognizes human CD48 and another substance having cellular cytotoxicity becomes a therapeutic agent effective for radical therapy for multiple myeloma.

Example 8

Figure 13:
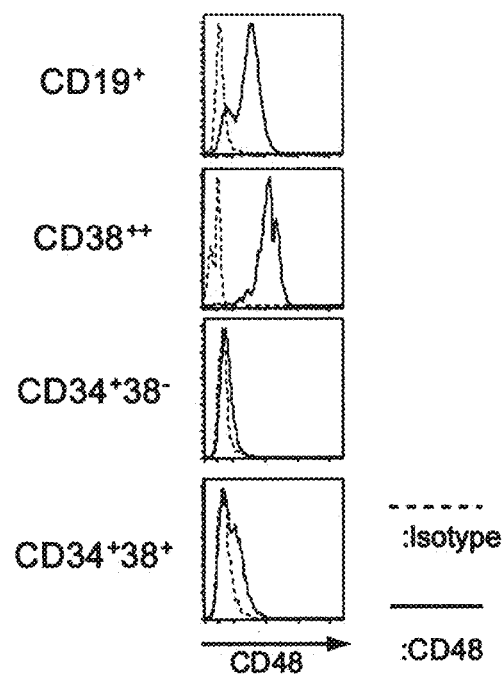
FIG. 13 shows a result of comparison of CD48 expression level in each of bone marrow cell fractions derived from a healthy subject.

Examination of Expression Level of CD48 in Normal Bone Marrow Hematopoietic Precursor Cells and Examination of CDC Activity of Anti-CD48 Antibody on Hematopoietic Precursor Cells As shown in FIG. 5, expression of CD48 is slightly observed in hematopoietic stem cells (CD34$^+$CD38$^-$) and CD34$^+$CD38$^-$ hematopoietic precursor cells. Also for bone marrow cells derived from a healthy subject, when the expression level of CD48 was checked similarly as in Example 3, expression of CD48 was confirmed at a very low level in CD34$^+$ cells that are fractions of hematopoietic stem cells and hematopoietic precursor cells (FIG. 13). Thus, it was examined whether hematopoietic stem cells and hematopoietic precursor cells are subjected to the cytotoxic effects by the anti-CD48 antibody as a result of expression of CD48 at such a low level.

Figure 14:
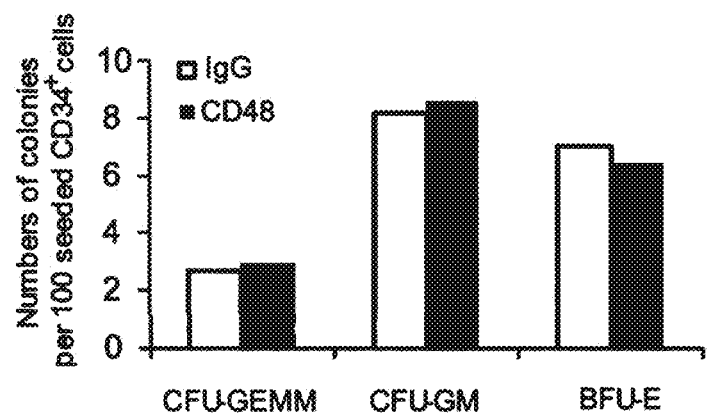
FIG. 14 shows the numbers of various kinds of colony forming cells obtained by cultivating CD34 positive hematopoietic precursor cells derived from a healthy subject in the presence of the anti-CD48 antibody (1B4) or mouse IgG and a complement.

Normal CD34$^+$ cells purified with CD34MACS beads (Miltenyi Biotec) were caused to react with the anti-human CD48 monoclonal antibody (1B4) and a complement by the same method as for the measurement of CDC activity, and then cultivated in a methylcellulose medium (Methocult H4334 (Stem Cell Technologies)), and the numbers of various colony forming cells were counted after 14 days. As a result, even with the cocultivation with the anti-CD48 antibody and the complement, the number of colonies formed from the normal hematopoietic precursor cells did not change at all (FIG. 14). The result demonstrates that the hematopoietic precursor cells are not subjected to cellular injury caused by the anti-CD48 antibody, and suggests that the anti-CD48 antibody is safe as a pharmaceutical agent.

Due to the above, targeting target cells in therapy for multiple myeloma using the anti-human CD48 monoclonal antibody is thought to be effective also in terms of safety.

Example 9

Identification of Myeloma Plasma Cells with Expression Level of CD48 as Marker

Figure 15:
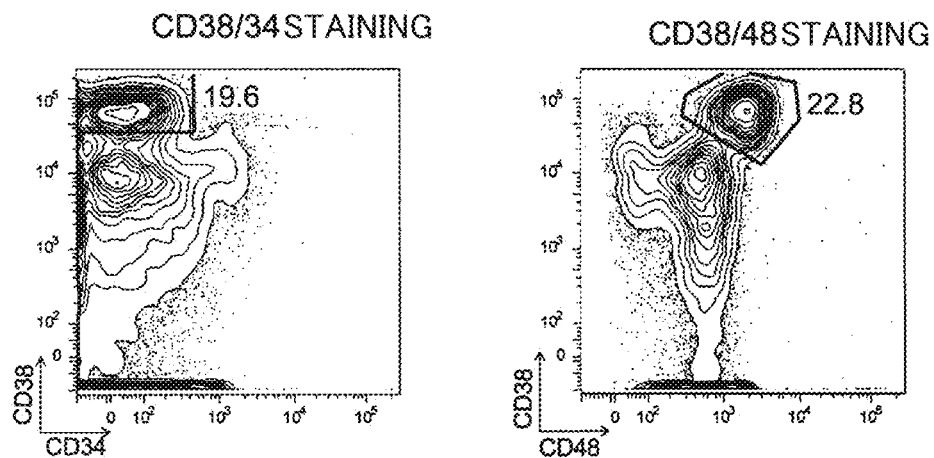
FIG. 15 shows a result of CD48-CD38 co-staining flow cytometry analysis for identifying myeloma cells in a myeloma patient.

As is obvious from FIGS. 4 and 5, the expression level of CD48 is very high in the myeloma precursor cells and the myeloma plasma cells. It is novel finding that CD48 has strong positivity for CD38-strong-positive myeloma cells. Using this, for myeloma patient bone marrow, CD48 and CD38 are co-stained and then analyzed by flow cytometry, whereby it is very easy to identify the myeloma cell population. One example of the analysis method is shown in FIG. 15. Use of CD48 as a marker together with CD38, which is in general used as a marker for myeloma cells, as in FIG. 15 allows the myeloma cell population to be identified very easily. CD38-strong-positive cells are normally identified as myeloma cells, but a level at which strong positivity is determined is arbitrary. Meanwhile, addition of CD48 as a marker allows the myeloma cell population to be regarded as a cell population having uniform and strong positivity for CD38 and CD48. The frequency, in bone marrow, of the myeloma cell population identified thus can be measured to recognize the degree of progression of myeloma.

The invention claimed is:

1. A method of treating multiple myeloma in a patient, comprising administrating to a patient having multiple myeloma an anti-human CD48 monoclonal antibody, wherein said treatment kills myeloma stem cells and/or myeloma precursor cells.

2. The method of claim 1, wherein the monoclonal antibody has cellular cytotoxicity.

3. The method of claim 1, wherein the monoclonal antibody is bound to a substance having cellular cytotoxicity.

4. The method of claim 1, wherein the monoclonal antibody has cellular cytotoxicity to cells expressing human CD48.

5. The method of claim 1, wherein the monoclonal antibody is a humanized antibody.

6. The method of claim 1, wherein said treatment also kills myeloma plasma cells.

7. A method of killing myeloma stem cells and/or myeloma precursor cells in a patient, comprising administering to a patient having multiple myeloma an anti-human CD48 monoclonal antibody.

8. The method of claim 7, wherein the monoclonal antibody has cellular cytotoxicity.

9. The method of claim 7, wherein the monoclonal antibody is bound to a substance having cellular cytotoxicity.

10. The method of claim 7, wherein the monoclonal antibody has cellular cytotoxicity to cells expressing human CD48.

11. The method of claim 7, wherein the monoclonal antibody is a humanized antibody.

12. The method of claim 7, wherein said method also kills myeloma plasma cells.

13. A method of killing myeloma stem cells, myeloma precursor cells, and myeloma plasma cells in a patient, comprising administrating to a patient having multiple myeloma an anti-human CD48 monoclonal antibody.

14. The method of claim 13, wherein the monoclonal antibody has cellular cytotoxicity.

15. The method of claim 13, wherein the monoclonal antibody is bound to a substance having cellular cytotoxicity.

16. The method of claim 13, wherein the monoclonal antibody has cellular cytotoxicity to cells expressing human CD48.

17. The method of claim 13, wherein the monoclonal antibody is a humanized antibody.

* * * * *

SEQUENCE LISTING

```
<160> NUMBER OF SEQ ID NOS: 8

<210> SEQ ID NO 1
<211> LENGTH: 118
<212> TYPE: PRT
<213> ORGANISM: Mus musculus

<400> SEQUENCE: 1

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Glu Arg Pro Gly His Gly Leu Glu Trp Ile
        35                  40                  45

Gly Asp Ile Tyr Pro Gly Gly Gly Phe Thr Asn Tyr Asn Glu Asn Phe
    50                  55                  60

Lys Gly Lys Ala Thr Leu Thr Ala Asp Thr Ser Ser Ser Thr Ala Tyr
```

```
                65                  70                  75                  80
Met Gln Leu Ser Ser Leu Thr Ser Glu Asp Ser Ala Ile Tyr His Cys
                    85                  90                  95

Ala Arg Gly Ile Tyr Tyr Asn Ser Ser Pro Tyr Phe Asp Ser Trp Gly
            100                 105                 110

Gln Gly Thr Thr Leu Thr
        115

<210> SEQ ID NO 2
<211> LENGTH: 354
<212> TYPE: DNA
<213> ORGANISM: Mus musculus

<400> SEQUENCE: 2
caggtccagc tgcagcagtc tggagctgag ctggtaaggc ctgggacttc agtgaagatg      60
tcctgcaagg ctgctggata caccttcact aactactgga taggttgggt aaaggagagg     120
cctggacatg gccttgagtg gattggagat atttaccctg aggtggctt tactaactac      180 aatgagaatt tcaagggcaa ggccacactg actgcagaca catcctccag cacagcctac     240
atgcagctca gcagcctgac atctgaggac tctgccatct atcactgtgc aagaggatt      300 tactacaata gtagccccta ctttgactcc tggggccaag gcaccactct caca            354

<210> SEQ ID NO 3
<211> LENGTH: 118
<212> TYPE: PRT
<213> ORGANISM: Mus musculus

<400> SEQUENCE: 3

Asp Ile Val Met Thr Gln Phe Ala Gly Val Asp Gly Asp Ile Val Met
1               5                   10                  15

Thr Gln Ser His Lys Phe Met Ser Thr Ser Val Gly Asp Arg Val Ser
                20                  25                  30

Ile Thr Cys Lys Ala Ser Gln Asp Val Ser Thr Val Ala Trp Tyr
            35                  40                  45

Gln Gln Lys Pro Gly Gln Ser Pro Lys Leu Leu Ile Tyr Ser Ala Tyr
50                  55                  60

Arg Tyr Thr Gly Val Pro Asp Arg Phe Thr Gly Ser Gly Ser Gly Thr
65                  70                  75                  80

Asp Phe Thr Phe Thr Ile Ser Ser Val Gln Ala Glu Asp Leu Ala Val
                85                  90                  95

Tyr Tyr Cys Gln Gln His Tyr Ser Thr Pro Pro Thr Phe Gly Gly Gly
            100                 105                 110

Thr Lys Leu Glu Ile Lys
        115

<210> SEQ ID NO 4
<211> LENGTH: 357
<212> TYPE: DNA
<213> ORGANISM: Mus musculus

<400> SEQUENCE: 4
gacattgtga tgacccagtt tgcaggtgtt gacggagaca ttgtgatgac ccagtctcac      60
aaattcatgt ccacatcagt aggagacagg gtcagcatca cctgcaaggc cagtcaggat     120
gtgagtacta ctgtggcctg gtatcagcag aaaccaggc aatctcctaa actactgatt      180
tattcggcat cctaccggta cactggagtc cctgatcgct tcactggcag tggatctggg     240
```

```
acggatttca ctttcaccat cagcagtgtg caggctgaag acctggcagt ttattactgt    300
cagcaacatt atagtactcc tcccacgttc ggaggggga ccaagctgga aataaaa        357
```

<210> SEQ ID NO 5
<211> LENGTH: 330
<212> TYPE: PRT
<213> ORGANISM: Mus musculus

<400> SEQUENCE: 5

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 6
<211> LENGTH: 107
<212> TYPE: PRT

<213> ORGANISM: Mus musculus

<400> SEQUENCE: 6

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 7
<211> LENGTH: 330
<212> TYPE: PRT
<213> ORGANISM: Homo sapiens

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 106
<212> TYPE: PRT
<213> ORGANISM: Homo sapiens

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```